(12) United States Patent
Warnking

(10) Patent No.: US 12,076,033 B2
(45) Date of Patent: Sep. 3, 2024

(54) ABLATION DEVICE WITH OPTIMIZED INPUT POWER PROFILE AND METHOD OF USING THE SAME

(71) Applicant: ReCor Medical, Inc., Palo Alto, CA (US)

(72) Inventor: Reinhard J. Warnking, East Setauket, NY (US)

(73) Assignee: Recor Medical, Inc., Palo Alto, CA (US)

( * ) Notice: Subject to any disclaimer, the term of this patent is extended or adjusted under 35 U.S.C. 154(b) by 406 days.

(21) Appl. No.: 16/701,047

(22) Filed: Dec. 2, 2019

(65) Prior Publication Data

US 2020/0170702 A1 Jun. 4, 2020

Related U.S. Application Data

(62) Division of application No. 12/227,508, filed as application No. PCT/US2007/011346 on May 10, 2007, now Pat. No. 10,499,937.

(Continued)

(51) Int. Cl.
*A61B 17/22* (2006.01)
*A61B 18/00* (2006.01)
(Continued)

(52) U.S. Cl.
CPC ........ *A61B 17/2202* (2013.01); *A61B 18/082* (2013.01); *A61B 18/1492* (2013.01);
(Continued)

(58) Field of Classification Search
CPC .............. A61B 17/2202; A61B 18/082; A61B 18/1492; A61B 2017/22024;
(Continued)

(56) References Cited

U.S. PATENT DOCUMENTS 3,168,659 A  2/1965 Bayre et al.
4,084,582 A  4/1978 Nigam
(Continued)

FOREIGN PATENT DOCUMENTS

DE  20 2005 022 060 U1  11/2012
EP  0659387  6/1995
(Continued)

OTHER PUBLICATIONS

Chen, Shih-Ann, M.D., "Initiation of Atrial Fibrillation by Ectopic Beats Originating From the Pulmonary Veins," Circulation 100(18): 1879-86, 1999.

(Continued)

*Primary Examiner* — Hien N Nguyen
(74) *Attorney, Agent, or Firm* — Theresa Ann Raymer

(57) ABSTRACT

Ablation device including a probe structure 10 having a proximal end 12 and a distal end 14. Probe structure 10 includes a tubular first catheter 16, a tubular second catheter 18 surrounding the first catheter and a tubular guide catheter extending within the first catheter 16. The first catheter 16 carries a cylindrical ultrasonic transducer 20 adjacent its distal end. The transducer 20 is connected to a source of electrical excitation. The ultrasonic waves emitted by the transducer 20 are directed at the heart wall tissue. Once the tissue reaches the target temperature, the electrical excitation is turned on and off to maintain the tissue at the largest temperature. Alternatively, the transducer 20 is subjected to continuous excitation at one power level and upon the tissue reaching the target temperature, the power level of the continuous excitation is switched to a second lower power level.

20 Claims, 4 Drawing Sheets

Related U.S. Application Data

(60) Provisional application No. 60/802,243, filed on May 19, 2006.

(51) Int. Cl.
*A61B 18/08* (2006.01)
*A61B 18/14* (2006.01)

(52) U.S. Cl.
CPC .............. A61B 2017/22024 (2013.01); A61B 2017/22051 (2013.01); A61B 2018/00244 (2013.01); A61B 2018/00351 (2013.01); A61B 2018/00702 (2013.01); A61B 2018/00714 (2013.01)

(58) Field of Classification Search
CPC ........... A61B 2017/22051; A61B 2018/00244; A61B 2018/00351; A61B 2018/00702; A61B 2018/00714
See application file for complete search history.

(56) References Cited

U.S. PATENT DOCUMENTS

| | | |
|---|---|---|
| 4,185,501 A | 1/1980 | Proudian et al. |
| 4,194,510 A | 3/1980 | Proudian |
| 4,338,942 A | 7/1982 | Forgarty |
| 4,387,720 A | 6/1983 | Miller |
| 4,391,281 A | 7/1983 | Green |
| 4,402,307 A | 9/1983 | Hanson et al. |
| 4,403,612 A | 9/1983 | Fogarty |
| 4,422,447 A | 12/1983 | Schiff |
| 4,433,692 A | 2/1984 | Baba |
| 4,643,186 A | 2/1987 | Rosen et al. |
| 4,650,466 A | 3/1987 | Luther |
| 4,672,961 A | 6/1987 | Davies |
| 4,680,499 A | 7/1987 | Umemura et al. |
| 4,685,334 A | 8/1987 | Latimer |
| 4,691,714 A | 9/1987 | Wong et al. |
| 4,709,698 A | 12/1987 | Johnston et al. |
| 4,722,347 A | 2/1988 | Abrams et al. |
| 4,744,366 A | 5/1988 | Jang |
| 4,785,815 A | 11/1988 | Cohen |
| 4,800,316 A | 1/1989 | Ju-Zhen |
| 4,813,934 A | 3/1989 | Engelson et al. |
| 4,841,977 A | 6/1989 | Griffith et al. |
| 4,842,977 A | 6/1989 | Griffith et al. |
| 4,869,263 A | 9/1989 | Segal et al. |
| 4,914,510 A | 4/1990 | Brennesholtz et al. |
| 4,945,912 A | 8/1990 | Langberg |
| 4,972,826 A | 11/1990 | Koehler et al. |
| 4,983,169 A | 1/1991 | Furukawa |
| 5,000,185 A | 3/1991 | Yock |
| 5,104,393 A | 4/1992 | Isner |
| 5,105,116 A | 4/1992 | Okamoto et al. |
| 5,114,423 A | 5/1992 | Kasprzyk |
| 5,117,831 A | 6/1992 | Jang et al. |
| 5,135,001 A | 8/1992 | Sinofsky et al. |
| 5,140,987 A | 8/1992 | Schuger |
| 5,160,336 A | 11/1992 | Favre |
| 5,167,233 A | 12/1992 | Eberle et al. |
| 5,209,299 A | 5/1993 | Ayres |
| 5,217,454 A | 6/1993 | Khoury |
| 5,226,421 A | 7/1993 | Frisbie et al. |
| 5,226,430 A | 7/1993 | Spears et al. |
| 5,240,005 A | 8/1993 | Viebach |
| 5,242,438 A | 9/1993 | Saadatmanesh et al. |
| 5,242,441 A | 9/1993 | Avitall |
| 5,246,438 A | 9/1993 | Langberg |
| 5,269,291 A | 12/1993 | Carter |
| 5,281,213 A | 1/1994 | Milder et al. |
| 5,281,218 A | 2/1994 | Imran |
| 5,293,868 A | 3/1994 | Nardella |
| 5,295,484 A | 3/1994 | Marcus et al. |
| 5,300,068 A | 4/1994 | Rosar et al. |
| 5,305,731 A | 4/1994 | Buchholtz |
| 5,305,755 A | 4/1994 | Nakao |
| 5,338,295 A | 8/1994 | Cornelius et al. |
| 5,342,292 A | 8/1994 | Nita et al. |
| 5,348,010 A | 9/1994 | Schnall et al. |
| 5,364,388 A | 11/1994 | Koziol |
| 5,368,591 A | 11/1994 | Lennox |
| 5,385,148 A | 1/1995 | Lesh et al. |
| 5,391,197 A | 2/1995 | Burdette et al. |
| 5,400,267 A | 3/1995 | Denen et al. |
| 5,415,654 A | 5/1995 | Daikuzono |
| 5,419,335 A | 5/1995 | Hartmann et al. |
| 5,421,338 A | 6/1995 | Crowley et al. |
| 5,423,319 A | 6/1995 | Seyed-Boloforosh |
| 5,423,755 A | 6/1995 | Kesten |
| 5,423,807 A | 6/1995 | Milder |
| 5,431,663 A | 7/1995 | Carter |
| 5,454,782 A | 10/1995 | Perkins |
| 5,456,259 A | 10/1995 | Barlow et al. |
| 5,468,239 A | 11/1995 | Tanner et al. |
| 5,471,988 A | 12/1995 | Fuijo |
| 5,477,736 A | 12/1995 | Lorraine |
| 5,488,955 A | 2/1996 | Dias |
| 5,492,532 A | 2/1996 | Ryan et al. |
| 5,513,639 A | 5/1996 | Satomi et al. |
| 5,558,672 A | 9/1996 | Edwards et al. |
| 5,562,720 A | 10/1996 | Stern et al. |
| 5,571,088 A | 11/1996 | Lennox et al. |
| 5,575,766 A | 11/1996 | Swartz et al. |
| 5,575,787 A | 11/1996 | Abela et al. |
| 5,575,788 A | 11/1996 | Baker et al. |
| 5,582,609 A | 12/1996 | Swanson et al. |
| 5,596,989 A | 1/1997 | Morita |
| 5,606,974 A | 3/1997 | Castellano et al. |
| 5,620,479 A | 4/1997 | Diedrich |
| 5,630,837 A | 5/1997 | Crowley |
| 5,643,279 A | 7/1997 | Trotta |
| 5,655,539 A | 8/1997 | Wang et al. |
| 5,657,755 A | 8/1997 | Desai |
| 5,669,932 A | 9/1997 | Fischell et al. |
| 5,676,692 A | 10/1997 | Sanghvi et al. |
| 5,688,266 A | 11/1997 | Edwards et al. |
| 5,693,043 A | 12/1997 | Kittrell et al. |
| 5,704,361 A | 1/1998 | Seward et al. |
| 5,707,352 A | 1/1998 | Sekins et al. |
| 5,720,287 A | 2/1998 | Chapelon et al. |
| 5,722,397 A | 3/1998 | Eppstein |
| 5,762,066 A | 6/1998 | Law et al. |
| 5,767,692 A | 6/1998 | Antonello et al. |
| 5,776,141 A | 7/1998 | Klein et al. |
| 5,800,392 A | 9/1998 | Racchini |
| 5,803,083 A | 9/1998 | Buck et al. |
| 5,817,018 A | 10/1998 | Ohtomo |
| 5,840,031 A | 11/1998 | Crowley |
| 5,840,066 A | 11/1998 | Matsuda et al. |
| 5,840,076 A | 11/1998 | Swanson et al. |
| 5,848,969 A | 12/1998 | Panescu et al. |
| 5,853,368 A | 12/1998 | Solomon et al. |
| 5,860,974 A | 1/1999 | Abele |
| 5,865,801 A | 2/1999 | Houser |
| 5,868,708 A | 2/1999 | Hart et al. |
| 5,868,779 A | 2/1999 | Ruiz |
| 5,891,135 A | 4/1999 | Jackson |
| 5,893,885 A | 4/1999 | Webster, Jr. |
| 5,916,170 A | 6/1999 | Kolz et al. |
| 5,916,213 A | 6/1999 | Haissaguerre et al. |
| 5,921,982 A | 7/1999 | Lesh et al. |
| 5,931,811 A | 8/1999 | Haissaguerre |
| 5,938,660 A | 8/1999 | Swartz et al. |
| 5,964,751 A | 10/1999 | Amplatz et al. |
| 5,971,968 A | 10/1999 | Tu et al. |
| 5,971,980 A * | 10/1999 | Sherman ............ A61B 18/1492 606/41 |
| 5,971,983 A | 10/1999 | Lesh |
| 6,002,955 A | 12/1999 | Willems et al. |
| 6,004,269 A | 12/1999 | Crowley et al. |
| 6,011,995 A | 1/2000 | Guglielmi et al. |
| 6,012,457 A | 1/2000 | Lesh |
| 6,013,053 A | 1/2000 | Bower et al. |

(56) References Cited

U.S. PATENT DOCUMENTS

| | | |
|---|---|---|
| 6,017,274 A | 1/2000 | Sherman et al. |
| 6,022,319 A | 2/2000 | Willard |
| 6,024,740 A | 2/2000 | Lesh et al. |
| 6,055,859 A | 5/2000 | Kozuka et al. |
| 6,056,744 A | 5/2000 | Edwards |
| 6,064,902 A | 5/2000 | Haissaguerre |
| 6,066,134 A | 5/2000 | Eggers et al. |
| 6,068,629 A | 5/2000 | Haissaguerre et al. |
| 6,071,279 A | 6/2000 | Whayne et al. |
| 6,073,052 A | 6/2000 | Zelickson et al. |
| 6,094,988 A | 8/2000 | Aindow |
| 6,096,054 A | 8/2000 | Wyzgala et al. |
| 6,097,985 A | 8/2000 | Kasevich et al. |
| 6,102,908 A | 8/2000 | Tu et al. |
| 6,106,474 A | 8/2000 | Koger et al. |
| 6,112,123 A | 8/2000 | Kelleher et al. |
| 6,117,101 A | 9/2000 | Diederich et al. |
| 6,123,456 A | 9/2000 | Lyons |
| 6,128,522 A | 10/2000 | Acker et al. |
| 6,146,379 A | 11/2000 | Fleischman |
| 6,152,144 A | 11/2000 | Lesh et al. |
| 6,152,920 A | 11/2000 | Thompson |
| 6,161,543 A | 12/2000 | Cox et al. |
| 6,163,716 A | 12/2000 | Edwards |
| 6,164,283 A | 12/2000 | Lesh |
| 6,166,092 A | 12/2000 | Sekins et al. |
| 6,183,492 B1 | 2/2001 | Hart et al. |
| 6,190,382 B1 | 2/2001 | Ormsby et al. |
| 6,193,713 B1 | 2/2001 | Geistert et al. |
| 6,196,059 B1 | 3/2001 | Kosslinger et al. |
| 6,197,023 B1 | 3/2001 | Muntermann |
| 6,200,269 B1 | 3/2001 | Lin et al. |
| 6,200,315 B1 | 3/2001 | Gaiser et al. |
| 6,203,525 B1 | 3/2001 | Whayne |
| 6,203,531 B1 | 3/2001 | Ockuly et al. |
| 6,206,831 B1 | 3/2001 | Suorsa et al. |
| 6,210,356 B1 | 4/2001 | Anderson et al. |
| 6,212,426 B1 | 4/2001 | Swanson |
| 6,216,704 B1 | 4/2001 | Ingle et al. |
| 6,217,576 B1 | 4/2001 | Tu et al. |
| 6,231,561 B1 | 5/2001 | Frazier et al. |
| 6,235,025 B1 | 5/2001 | Swartz et al. |
| 6,237,605 B1 | 5/2001 | Vaska et al. |
| 6,238,335 B1 | 5/2001 | Silverman et al. |
| 6,241,754 B1 | 6/2001 | Swanson et al. |
| 6,245,064 B1 | 6/2001 | Lesh et al. |
| 6,251,109 B1 | 6/2001 | Hassett et al. |
| 6,254,598 B1 | 7/2001 | Edwards |
| 6,254,599 B1 | 7/2001 | Lesh et al. |
| 6,280,402 B1 | 8/2001 | Ishibashi et al. |
| 6,282,949 B1 | 9/2001 | Axelsson |
| 6,283,127 B1 | 9/2001 | Sterman et al. |
| 6,283,989 B1 | 9/2001 | Laufer et al. |
| 6,290,674 B1 | 9/2001 | Roue et al. |
| 6,292,695 B1 | 9/2001 | Webster |
| 6,296,619 B1 | 10/2001 | Brisken et al. |
| 6,302,875 B1 | 10/2001 | Makower et al. |
| 6,305,378 B1 | 10/2001 | Lesh |
| 6,306,133 B1 | 10/2001 | Tu et al. |
| 6,311,692 B1 | 11/2001 | Vaska et al. |
| 6,314,325 B1 | 11/2001 | Fitz |
| 6,314,962 B1 | 11/2001 | Vaska et al. |
| 6,314,963 B1 | 11/2001 | Vaska et al. |
| 6,315,778 B1 | 11/2001 | Gambale et al. |
| 6,321,121 B1 | 11/2001 | Zelkickson et al. |
| 6,330,473 B1 | 12/2001 | Swanson et al. |
| 6,332,880 B1 | 12/2001 | Yang et al. |
| 6,355,030 B1 | 3/2002 | Aldrich et al. |
| 6,355,051 B1 | 3/2002 | Sisskind et al. |
| 6,383,151 B1 | 5/2002 | Diederich et al. |
| 6,398,792 B1 | 6/2002 | O'Connor |
| 6,405,732 B1 | 6/2002 | Edwards et al. |
| 6,423,026 B1 | 7/2002 | Gesswein et al. |
| 6,461,314 B1 | 10/2002 | Pant et al. |
| 6,475,146 B1 | 11/2002 | Frelburger et al. |
| 6,485,489 B2 | 11/2002 | Teirstein et al. |
| 6,491,710 B2 | 12/2002 | Satake |
| 6,492,762 B1 | 12/2002 | Pant et al. |
| 6,500,174 B1 | 12/2002 | Maguire et al. |
| 6,508,774 B1 | 1/2003 | Acker et al. |
| 6,513,385 B1 | 2/2003 | Han et al. |
| 6,514,246 B1 | 2/2003 | Swanson et al. |
| 6,514,249 B1 | 2/2003 | Maguire et al. |
| 6,517,536 B2 | 2/2003 | Hooven et al. |
| 6,529,756 B1 | 3/2003 | Phan |
| 6,540,744 B2 | 4/2003 | Hassett et al. |
| 6,542,251 B2 | 4/2003 | Mueller-Rentz |
| 6,543,271 B2 | 4/2003 | Herrmann et al. |
| 6,543,274 B1 | 4/2003 | Herrmann et al. |
| 6,564,096 B2 | 5/2003 | Mest |
| 6,589,274 B2 | 7/2003 | Stiger et al. |
| 6,599,256 B1 | 7/2003 | Acker et al. |
| 6,599,288 B2 | 7/2003 | Maguire et al. |
| 6,607,476 B1 | 8/2003 | Barnhart |
| 6,607,502 B1 | 8/2003 | Maguire et al. |
| 6,626,861 B1 | 9/2003 | Hart et al. |
| 6,626,899 B2 | 9/2003 | Houser et al. |
| 6,635,054 B2 | 10/2003 | Fjield et al. |
| 6,641,579 B1 | 11/2003 | Bernardi et al. |
| 6,642,515 B1 | 11/2003 | Yamaguchi |
| 6,645,199 B1 | 11/2003 | Jenkens et al. |
| 6,645,202 B1 | 11/2003 | Pless et al. |
| 6,652,515 B1 | 11/2003 | Maguire et al. |
| 6,652,547 B2 | 11/2003 | Rabiner et al. |
| 6,656,174 B1 | 12/2003 | Hegde et al. |
| 6,658,279 B2 | 12/2003 | Swanson et al. |
| 6,660,013 B2 | 12/2003 | Rabiner et al. |
| 6,669,638 B1 | 12/2003 | Miller et al. |
| 6,669,655 B1 | 12/2003 | Acker |
| 6,669,687 B1 | 12/2003 | Saadat |
| 6,672,312 B2 | 1/2004 | Acker |
| 6,692,490 B1 | 2/2004 | Edwards |
| 6,695,782 B2 | 2/2004 | Ranucci et al. |
| 6,719,755 B2 | 4/2004 | Sliwa, Jr. et al. |
| 6,733,451 B2 | 5/2004 | Rabiner et al. |
| 6,740,040 B1 | 5/2004 | Mandrusov |
| 6,740,082 B2 | 5/2004 | Shadduck |
| 6,740,107 B2 | 5/2004 | Loeb et al. |
| 6,763,722 B2 | 7/2004 | Fjield et al. |
| 6,764,486 B2 | 7/2004 | Natale |
| 6,808,524 B2 | 10/2004 | Lopath et al. |
| 6,837,886 B2 | 1/2005 | Collins |
| 6,840,936 B2 | 1/2005 | Sliwa et al. |
| 6,845,267 B2 | 1/2005 | Harrison et al. |
| 6,866,760 B2 | 3/2005 | Paolini, Jr. et al. |
| 6,929,608 B1 | 8/2005 | Hutchinson et al. |
| 6,954,977 B2 | 10/2005 | Maguire |
| 6,964,660 B2 | 11/2005 | Maguire et al. |
| 6,964,751 B2 | 11/2005 | Storm et al. |
| 6,966,908 B2 | 11/2005 | Maguire et al. |
| 6,976,492 B2 | 12/2005 | Ingle et al. |
| 6,997,925 B2 | 2/2006 | Maguire et al. |
| 7,052,695 B2 | 5/2006 | Kalish |
| 7,082,336 B2 | 7/2006 | Ransbury et al. |
| 7,083,614 B2 | 8/2006 | Fjield et al. |
| 7,137,963 B2 | 11/2006 | Nita et al. |
| 7,156,816 B2 | 1/2007 | Schwartz et al. |
| 7,162,303 B2 | 1/2007 | Levin et al. |
| 7,189,229 B2 | 3/2007 | Lopath et al. |
| 7,217,284 B2 | 5/2007 | Houser et al. |
| 7,229,469 B1 | 6/2007 | Witzel et al. |
| 7,269,453 B2 | 9/2007 | Mogul |
| 7,311,701 B2 | 12/2007 | Gifford et al. |
| 7,326,201 B2 | 2/2008 | Fjield et al. |
| 7,340,307 B2 | 3/2008 | Maguire et al. |
| 7,347,852 B2 | 3/2008 | Hobbs et al. |
| 7,371,231 B2 | 5/2008 | Rioux et al. |
| 7,503,895 B2 | 3/2009 | Rabiner et al. |
| 7,529,582 B1 | 5/2009 | DiLorenzo |
| 7,529,589 B2 | 5/2009 | Williams et al. |
| 7,532,938 B2 | 5/2009 | Machado et al. |
| 7,573,182 B2 | 8/2009 | Savage |
| 7,591,996 B2 | 9/2009 | Hwang et al. |
| 7,599,736 B2 | 10/2009 | DiLorenzo |

(56) References Cited

U.S. PATENT DOCUMENTS

| | | |
|---|---|---|
| 7,617,005 B2 | 11/2009 | Demarais et al. |
| 7,621,902 B2 | 11/2009 | Nita et al. |
| 7,625,371 B2 | 12/2009 | Morris et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,725,196 B2 | 5/2010 | Machado et al. |
| 7,795,293 B2 | 9/2010 | Moore |
| 7,837,676 B2 | 11/2010 | Sinelnikov et al. |
| 7,925,352 B2 | 4/2011 | Stack et al. |
| 7,942,871 B2 | 5/2011 | Thapliyal et al. |
| 8,024,050 B2 | 9/2011 | Libbus et al. |
| 8,025,688 B2 | 9/2011 | Diederich et al. |
| 8,040,612 B2 | 10/2011 | Suijver et al. |
| 8,088,127 B2 | 1/2012 | Mayse et al. |
| 8,116,883 B2 | 2/2012 | Williams et al. |
| 8,131,371 B2 | 3/2012 | Demarals et al. |
| 8,137,274 B2 | 3/2012 | Weng et al. |
| 8,140,170 B2 | 3/2012 | Rezai et al. |
| 8,150,518 B2 | 4/2012 | Levin et al. |
| 8,155,744 B2 | 4/2012 | Rezai |
| 8,233,221 B2 | 7/2012 | Suijver et al. |
| 8,251,986 B2 | 8/2012 | Chornenky et al. |
| 8,287,472 B2 | 10/2012 | Ostrovsky et al. |
| 8,447,414 B2 | 5/2013 | Johnson et al. |
| 8,475,442 B2 | 7/2013 | Hall et al. |
| 8,483,831 B1 | 7/2013 | Hiavka et al. |
| 8,485,993 B2 | 7/2013 | Orszulak et al. |
| 8,504,147 B2 | 8/2013 | Deem et al. |
| D697,036 S | 1/2014 | Kay et al. |
| 8,626,300 B2 | 1/2014 | Demarais et al. |
| 8,702,619 B2 | 4/2014 | Wang |
| 8,715,209 B2 | 5/2014 | Gertner |
| 8,734,438 B2 | 5/2014 | Behnke |
| D708,810 S | 7/2014 | Lewis, Jr. |
| 8,774,913 B2 | 7/2014 | Demarais et al. |
| 8,790,281 B2 | 7/2014 | Diederich et al. |
| 8,808,345 B2 | 8/2014 | Clark et al. |
| 8,818,514 B2 | 8/2014 | Zarins et al. |
| D712,352 S | 9/2014 | George et al. |
| D712,353 S | 9/2014 | George et al. |
| D712,833 S | 9/2014 | George et al. |
| 8,845,629 B2 | 9/2014 | Demarais et al. |
| 8,932,289 B2 | 1/2015 | Mayse et al. |
| 8,974,445 B2 | 3/2015 | Warnking et al. |
| 9,022,948 B2 | 5/2015 | Wang |
| 9,028,472 B2 | 5/2015 | Mathur et al. |
| 9,066,720 B2 | 6/2015 | Ballakur et al. |
| 9,072,902 B2 | 7/2015 | Mathur et al. |
| 9,155,590 B2 | 10/2015 | Mathur |
| 9,186,198 B2 | 10/2015 | Demarais et al. |
| 9,186,212 B2 | 11/2015 | Nabulovsky et al. |
| 9,289,132 B2 | 3/2016 | Ghaffari |
| 9,326,816 B2 | 5/2016 | Srivastava |
| 9,327,123 B2 | 5/2016 | Yamasaki |
| 9,333,035 B2 | 5/2016 | Rudie |
| 9,339,332 B2 | 5/2016 | Srivastava |
| 9,345,530 B2 | 5/2016 | Ballakur et al. |
| 9,375,154 B2 | 6/2016 | Wang |
| 9,427,579 B2 | 8/2016 | Fain et al. |
| 9,439,598 B2 | 9/2016 | Shimada et al. |
| 9,649,064 B2 | 5/2017 | Toth et al. |
| 9,723,998 B2 | 8/2017 | Wang |
| 9,730,639 B2 | 8/2017 | Toth et al. |
| 9,743,845 B2 | 8/2017 | Wang |
| 9,750,560 B2 | 9/2017 | Ballakur et al. |
| 9,770,291 B2 | 9/2017 | Wang et al. |
| 9,770,593 B2 | 9/2017 | Gross |
| 9,801,684 B2 | 10/2017 | Fain |
| 9,820,811 B2 | 11/2017 | Wang |
| 9,907,983 B2 | 3/2018 | Thapliyal et al. |
| 9,931,047 B2 | 4/2018 | Srivastava |
| 9,943,666 B2 | 4/2018 | Warnking |
| 9,956,034 B2 | 5/2018 | Toth et al. |
| 9,968,790 B2 | 5/2018 | Toth et al. |
| 9,981,108 B2 | 5/2018 | Warnking |
| 9,999,463 B2 | 6/2018 | Puryear et al. |
| 10,004,458 B2 | 6/2018 | Toth et al. |
| 10,004,557 B2 | 6/2018 | Gross et al. |
| 10,010,364 B2 | 7/2018 | Harringtpm |
| 10,016,233 B2 | 7/2018 | Pike |
| 10,022,085 B2 | 7/2018 | Toth et al. |
| 10,039,901 B2 | 8/2018 | Warnking |
| 10,123,903 B2 | 11/2018 | Warnking et al. |
| 10,143,419 B2 | 12/2018 | Toth et al. |
| 10,179,020 B2 | 1/2019 | Ballakur et al. |
| 10,179,026 B2 | 1/2019 | Ng |
| 10,182,865 B2 | 1/2019 | Naga et al. |
| 10,226,633 B2 | 3/2019 | Toth et al. |
| 10,245,429 B2 | 4/2019 | Deem et al. |
| 10,292,610 B2 | 5/2019 | Srivastava |
| 10,293,190 B2 | 5/2019 | Zarins et al. |
| 10,363,359 B2 | 7/2019 | Toth et al. |
| 10,368,775 B2 | 8/2019 | Hettrick et al. |
| 10,376,310 B2 | 8/2019 | Fain et al. |
| 10,383,685 B2 | 8/2019 | Gross et al. |
| 10,398,332 B2 | 9/2019 | Min et al. |
| 10,470,684 B2 | 11/2019 | Toth et al. |
| 10,478,249 B2 | 11/2019 | Gross et al. |
| 10,543,037 B2 | 1/2020 | Shah |
| 10,850,091 B2 | 12/2020 | Zarins et al. |
| 11,801,085 B2 | 10/2023 | Wu et al. |
| 2001/0007070 A1 | 7/2001 | Stewart et al. |
| 2001/0007940 A1 | 7/2001 | Tu et al. |
| 2001/0023365 A1 | 9/2001 | Medhkour et al. |
| 2002/0019627 A1 | 2/2002 | Maguire et al. |
| 2002/0042610 A1 | 4/2002 | Sliwa, Jr. et al. |
| 2002/0062123 A1 | 5/2002 | McClurken et al. |
| 2002/0065512 A1 | 5/2002 | Fjield et al. |
| 2002/0068885 A1 | 6/2002 | Harhen et al. |
| 2002/0072741 A1 | 6/2002 | Sliwa, Jr. et al. |
| 2002/0087156 A1 | 7/2002 | Maguire et al. |
| 2002/0151889 A1 | 10/2002 | Swanson et al. |
| 2002/0165535 A1 | 11/2002 | Lesh et al. |
| 2002/0173724 A1 | 11/2002 | Dorando et al. |
| 2002/0193681 A1 | 12/2002 | Vitek et al. |
| 2003/0004439 A1 | 1/2003 | Pant et al. |
| 2003/0013968 A1 | 1/2003 | Fjield et al. |
| 2003/0028111 A1 | 2/2003 | Vaezy et al. |
| 2003/0036705 A1 | 2/2003 | Hare et al. |
| 2003/0050632 A1 | 3/2003 | Fjield et al. |
| 2003/0050637 A1 | 3/2003 | Maguire et al. |
| 2003/0065263 A1 | 4/2003 | Hare et al. |
| 2003/0074039 A1 | 4/2003 | Puskas |
| 2003/0114901 A1 | 6/2003 | Loeb et al. |
| 2003/0125726 A1 | 7/2003 | Maguire et al. |
| 2003/0181963 A1 | 9/2003 | Pellegrino et al. |
| 2003/0204138 A1 | 10/2003 | Choi |
| 2003/0216721 A1 | 11/2003 | Diederich et al. |
| 2003/0216792 A1 | 11/2003 | Levin |
| 2003/0225331 A1 | 12/2003 | Diederich et al. |
| 2003/0233099 A1 | 12/2003 | Danaek et al. |
| 2003/0236539 A1 | 12/2003 | Rabiner et al. |
| 2004/0019349 A1 | 1/2004 | Fuimaono et al. |
| 2004/0054362 A1 | 3/2004 | Lopath et al. |
| 2004/0068257 A1 | 4/2004 | Lopath et al. |
| 2004/0082859 A1 | 4/2004 | Schaer |
| 2004/0097819 A1 | 5/2004 | Duarte |
| 2004/0097996 A1 | 5/2004 | Rabiner et al. |
| 2004/0106880 A1 | 6/2004 | Weng et al. |
| 2004/0122494 A1 | 6/2004 | Eggers et al. |
| 2004/0158151 A1 | 8/2004 | Ranucci et al. |
| 2004/0176757 A1 | 9/2004 | Sinelnikov et al. |
| 2004/0181178 A1 | 9/2004 | Aldrich et al. |
| 2004/0242999 A1 | 12/2004 | Vitek et al. |
| 2005/0038340 A1 | 2/2005 | Vaezy et al. |
| 2005/0159738 A1 | 7/2005 | Visram et al. |
| 2005/0165391 A1 | 7/2005 | Maguire et al. |
| 2005/0171524 A1 | 8/2005 | Stern et al. |
| 2005/0203501 A1 | 9/2005 | Aldrich et al. |
| 2005/0209588 A1 | 9/2005 | Larson et al. |
| 2005/0209621 A1* | 9/2005 | Gordon ............... A61M 3/0216 606/167 |
| 2005/0215990 A1 | 9/2005 | Govari |

(56) References Cited

U.S. PATENT DOCUMENTS

| | | |
|---|---|---|
| 2005/0228283 A1 | 10/2005 | Gifford et al. |
| 2005/0228459 A1 | 10/2005 | Levin et al. |
| 2005/0228460 A1 | 10/2005 | Levin et al. |
| 2005/0234523 A1 | 10/2005 | Levin et al. |
| 2005/0251127 A1 | 11/2005 | Brosch et al. |
| 2005/0256518 A1 | 11/2005 | Rama et al. |
| 2005/0288730 A1 | 12/2005 | Deem et al. |
| 2006/0009753 A1 | 1/2006 | Fjield et al. |
| 2006/0025756 A1* | 2/2006 | Francischelli .......... A61N 7/02 606/27 |
| 2006/0041277 A1 | 2/2006 | Deem et al. |
| 2006/0052695 A1 | 3/2006 | Adam et al. |
| 2006/0057560 A1 | 3/2006 | Hlavka et al. |
| 2006/0058711 A1 | 3/2006 | Harhen et al. |
| 2006/0064081 A1 | 3/2006 | Rosinko |
| 2006/0118127 A1 | 6/2006 | Chinn |
| 2006/0142827 A1 | 6/2006 | Willard et al. |
| 2006/0184069 A1 | 8/2006 | Vaitekunas |
| 2006/0206028 A1 | 9/2006 | Lee et al. |
| 2006/0212076 A1 | 9/2006 | Demarais et al. |
| 2006/0212078 A1 | 9/2006 | Demarais et al. |
| 2006/0217772 A1 | 9/2006 | Libbus et al. |
| 2006/0235286 A1 | 10/2006 | Stone et al. |
| 2006/0241524 A1 | 10/2006 | Lee et al. |
| 2006/0265014 A1 | 11/2006 | Demarais et al. |
| 2006/0270975 A1 | 11/2006 | Savage |
| 2006/0270976 A1 | 11/2006 | Savage et al. |
| 2006/0276852 A1 | 12/2006 | Demarais et al. |
| 2007/0060921 A1 | 3/2007 | Janssen et al. |
| 2007/0072741 A1 | 3/2007 | Robideau |
| 2007/0083239 A1 | 4/2007 | Demarais et al. |
| 2007/0106292 A1 | 5/2007 | Kaplan |
| 2007/0135875 A1 | 6/2007 | Demarais et al. |
| 2007/0173899 A1 | 7/2007 | Levin et al. |
| 2007/0249046 A1 | 10/2007 | Shields |
| 2007/0255267 A1 | 11/2007 | Diederich et al. |
| 2007/0265609 A1 | 11/2007 | Thapliyal et al. |
| 2007/0265610 A1 | 11/2007 | Thapliyal et al. |
| 2007/0282407 A1 | 12/2007 | Demarais et al. |
| 2008/0027505 A1 | 1/2008 | Levin et al. |
| 2008/0039746 A1 | 2/2008 | Hissong et al. |
| 2008/0082859 A1 | 4/2008 | Kondo |
| 2008/0108988 A1 | 5/2008 | Edwards |
| 2008/0172049 A1 | 7/2008 | Bredno et al. |
| 2008/0172104 A1 | 7/2008 | Kieval et al. |
| 2008/0195092 A1 | 8/2008 | Kim et al. |
| 2008/0215031 A1 | 9/2008 | Belfort et al. |
| 2008/0255449 A1 | 10/2008 | Warnking et al. |
| 2008/0300588 A1 | 12/2008 | Groth et al. |
| 2009/0149753 A1 | 6/2009 | Govari et al. |
| 2009/0171202 A1 | 7/2009 | Kirkpatrick et al. |
| 2009/0198223 A1 | 8/2009 | Thilwind et al. |
| 2009/0216286 A1 | 8/2009 | DiLorenzo |
| 2009/0221939 A1 | 9/2009 | Demarais et al. |
| 2009/0228003 A1 | 9/2009 | Sinelnikov |
| 2009/0234407 A1 | 9/2009 | Hastings et al. |
| 2009/0248005 A1 | 10/2009 | Rusin et al. |
| 2009/0306739 A1 | 12/2009 | DiLorenzo |
| 2009/0312673 A1 | 12/2009 | Thapliyal et al. |
| 2009/0312693 A1 | 12/2009 | Thapliyal et al. |
| 2009/0312755 A1 | 12/2009 | Thapliyal et al. |
| 2010/0004528 A1 | 1/2010 | Weiss et al. |
| 2010/0010567 A1 | 1/2010 | Deem et al. |
| 2010/0016762 A1 | 1/2010 | Thapliyal et al. |
| 2010/0016934 A1 | 1/2010 | David et al. |
| 2010/0037902 A1 | 2/2010 | Wirtz et al. |
| 2010/0041977 A1 | 2/2010 | Lips et al. |
| 2010/0049099 A1 | 2/2010 | Thapliyal et al. |
| 2010/0063492 A1 | 3/2010 | Kahlert et al. |
| 2010/0113928 A1 | 5/2010 | Thapliyal et al. |
| 2010/0113985 A1 | 5/2010 | Thapliyal et al. |
| 2010/0114094 A1 | 5/2010 | Thapliyal et al. |
| 2010/0125198 A1 | 5/2010 | Thapliyal et al. |
| 2010/0152582 A1 | 6/2010 | Thapliyal et al. |
| 2010/0171394 A1 | 7/2010 | Glenn et al. |
| 2010/0185126 A1 | 7/2010 | Hall et al. |
| 2010/0191112 A1 | 7/2010 | Demarais et al. |
| 2010/0198065 A1 | 8/2010 | Thapliyal et al. |
| 2010/0211131 A1 | 8/2010 | Williams et al. |
| 2010/0249888 A1 | 9/2010 | Glenn et al. |
| 2010/0259832 A1 | 10/2010 | Suijver et al. |
| 2010/0262130 A1 | 10/2010 | Mihajlovic et al. |
| 2010/0272398 A1 | 10/2010 | Mihajlovic et al. |
| 2010/0274235 A1 | 10/2010 | Mihajlovic et al. |
| 2010/0280504 A1 | 11/2010 | Manzke et al. |
| 2010/0290318 A1 | 11/2010 | Kuiper et al. |
| 2011/0028798 A1 | 2/2011 | Hyde et al. |
| 2011/0029038 A1 | 2/2011 | Hyde et al. |
| 2011/0029044 A1 | 2/2011 | Hyde et al. |
| 2011/0079230 A1 | 4/2011 | Danek et al. |
| 2011/0087096 A1 | 4/2011 | Behar |
| 2011/0087097 A1 | 4/2011 | Behar |
| 2011/0104060 A1 | 5/2011 | Seward |
| 2011/0104061 A1 | 5/2011 | Seward |
| 2011/0118714 A1 | 5/2011 | Deladi et al. |
| 2011/0118723 A1 | 5/2011 | Turner et al. |
| 2011/0118725 A1 | 5/2011 | Mayse et al. |
| 2011/0125206 A1 | 5/2011 | Bornzin |
| 2011/0130663 A1 | 6/2011 | Raju et al. |
| 2011/0163630 A1 | 7/2011 | Klootwijk et al. |
| 2011/0166482 A1 | 7/2011 | Stack et al. |
| 2011/0172527 A1 | 7/2011 | Gertner |
| 2011/0178516 A1 | 7/2011 | Orszulak et al. |
| 2011/0207758 A1 | 8/2011 | Sobotka et al. |
| 2011/0208096 A1 | 8/2011 | Demarais et al. |
| 2011/0208173 A1 | 8/2011 | Sobotka et al. |
| 2011/0208175 A1 | 8/2011 | Sobotka et al. |
| 2011/0237983 A1 | 9/2011 | Nita et al. |
| 2011/0257512 A1 | 10/2011 | Krueger |
| 2011/0257523 A1 | 10/2011 | Hastings et al. |
| 2011/0257561 A1 | 10/2011 | Gertner et al. |
| 2011/0257563 A1 | 10/2011 | Thapliyal et al. |
| 2011/0257564 A1 | 10/2011 | Demarais et al. |
| 2011/0257641 A1 | 10/2011 | Hastings et al. |
| 2011/0257647 A1 | 10/2011 | Mayse et al. |
| 2011/0263921 A1 | 10/2011 | Vrba et al. |
| 2011/0264086 A1 | 10/2011 | Ingle |
| 2011/0270238 A1 | 11/2011 | Rizq et al. |
| 2011/0275962 A1 | 11/2011 | Deladi et al. |
| 2011/0301508 A1 | 12/2011 | Sethuraman et al. |
| 2011/0313290 A1 | 12/2011 | Weekamp et al. |
| 2011/0319765 A1 | 12/2011 | Gertner et al. |
| 2012/0004547 A1 | 1/2012 | Harks et al. |
| 2012/0004656 A1 | 1/2012 | Jackson et al. |
| 2012/0016358 A1 | 1/2012 | Mayse et al. |
| 2012/0022409 A1 | 1/2012 | Gertner et al. |
| 2012/0029509 A1 | 2/2012 | Smith |
| 2012/0059286 A1 | 3/2012 | Hastings et al. |
| 2012/0059431 A1 | 3/2012 | Williams et al. |
| 2012/0065492 A1 | 3/2012 | Gertner et al. |
| 2012/0065493 A1 | 3/2012 | Gertner |
| 2012/0065494 A1 | 3/2012 | Gertner et al. |
| 2012/0065506 A1 | 3/2012 | Smith |
| 2012/0065554 A1 | 3/2012 | Pikus |
| 2012/0089047 A1 | 4/2012 | Ryba et al. |
| 2012/0095461 A1 | 4/2012 | Herscher et al. |
| 2012/0109018 A1 | 5/2012 | Gertner et al. |
| 2012/0109021 A1 | 5/2012 | Hastings et al. |
| 2012/0116392 A1 | 5/2012 | Willard |
| 2012/0123243 A1 | 5/2012 | Hastings |
| 2012/0123261 A1 | 5/2012 | Jenson et al. |
| 2012/0123303 A1 | 5/2012 | Sogard et al. |
| 2012/0123406 A1 | 5/2012 | Edmunds et al. |
| 2012/0143097 A1 | 6/2012 | Pike, Jr. |
| 2012/0165667 A1 | 6/2012 | Altmann et al. |
| 2012/0172723 A1 | 7/2012 | Gertner |
| 2012/0232436 A1 | 9/2012 | Warnking |
| 2012/0238918 A1 | 9/2012 | Gertner |
| 2012/0238919 A1 | 9/2012 | Gertner |
| 2012/0265198 A1 | 10/2012 | Crow et al. |
| 2012/0296232 A1 | 11/2012 | Ng |
| 2012/0307034 A1 | 12/2012 | Sekine |
| 2012/0316439 A1 | 12/2012 | Behar |
| 2013/0012844 A1 | 1/2013 | Demarais et al. |

(56) References Cited

U.S. PATENT DOCUMENTS

| | | |
|---|---|---|
| 2013/0023897 A1 | 1/2013 | Wallace |
| 2013/0072928 A1 | 3/2013 | Schaer |
| 2013/0085489 A1 | 4/2013 | Fain et al. |
| 2013/0090650 A1 | 4/2013 | Jenson et al. |
| 2013/0096550 A1 | 4/2013 | Hill |
| 2013/0103064 A1 | 4/2013 | Arenson et al. |
| 2013/0110012 A1 | 5/2013 | Gertner |
| 2013/0116737 A1 | 5/2013 | Edwards et al. |
| 2013/0123770 A1 | 5/2013 | Smith |
| 2013/0131668 A1 | 5/2013 | Schaer |
| 2013/0131743 A1 | 5/2013 | Yamasaki et al. |
| 2013/0138018 A1 | 5/2013 | Gertner |
| 2013/0150749 A1 | 6/2013 | McLean et al. |
| 2013/0158441 A1 | 6/2013 | Demarais et al. |
| 2013/0158442 A1 | 6/2013 | Demarais et al. |
| 2013/0165822 A1 | 6/2013 | Demarais et al. |
| 2013/0165924 A1 | 6/2013 | Mathur et al. |
| 2013/0165925 A1 | 6/2013 | Mathur et al. |
| 2013/0197555 A1 | 8/2013 | Schaer |
| 2013/0204167 A1 | 8/2013 | Sverdlik et al. |
| 2013/0211396 A1 | 8/2013 | Sverdlik et al. |
| 2013/0211437 A1 | 8/2013 | Sverdlik et al. |
| 2013/0218054 A1 | 8/2013 | Sverdlik et al. |
| 2013/0274614 A1 | 10/2013 | Shimada et al. |
| 2013/0274658 A1 | 10/2013 | Steinke et al. |
| 2013/0282084 A1 | 10/2013 | Mathur et al. |
| 2013/0289369 A1 | 10/2013 | Margolis |
| 2013/0289682 A1 | 10/2013 | Barman et al. |
| 2013/0304047 A1 | 11/2013 | Grunewald et al. |
| 2013/0331739 A1 | 12/2013 | Gertner |
| 2014/0012133 A1 | 1/2014 | Sverdlik et al. |
| 2014/0018788 A1 | 1/2014 | Engelman et al. |
| 2014/0018794 A1 | 1/2014 | Anderson et al. |
| 2014/0025069 A1 | 1/2014 | Willard et al. |
| 2014/0031727 A1 | 1/2014 | Warnking |
| 2014/0039477 A1 | 2/2014 | Sverdlik et al. |
| 2014/0046313 A1 | 2/2014 | Pederson et al. |
| 2014/0058294 A1 | 2/2014 | Gross et al. |
| 2014/0067029 A1 | 3/2014 | Schauer et al. |
| 2014/0074083 A1 | 3/2014 | Horn et al. |
| 2014/0078794 A1 | 3/2014 | Fujii |
| 2014/0107639 A1 | 4/2014 | Zhang et al. |
| 2014/0163540 A1 | 6/2014 | Iyer et al. |
| 2014/0180196 A1 | 6/2014 | Stone et al. |
| 2014/0180197 A1 | 6/2014 | Sverdlik et al. |
| 2014/0194785 A1 | 7/2014 | Gertner |
| 2014/0200489 A1 | 7/2014 | Behar et al. |
| 2014/0214018 A1 | 7/2014 | Behar et al. |
| 2014/0249524 A1 | 9/2014 | Kocur |
| 2014/0257271 A1 | 9/2014 | Mayse et al. |
| 2014/0272110 A1 | 9/2014 | Taylor et al. |
| 2014/0274614 A1 | 9/2014 | Min et al. |
| 2014/0275924 A1 | 9/2014 | Min et al. |
| 2014/0276742 A1 | 9/2014 | Nabutovsky et al. |
| 2014/0276752 A1 | 9/2014 | Wang et al. |
| 2014/0276755 A1 | 9/2014 | Cao et al. |
| 2014/0276789 A1 | 9/2014 | Dandler et al. |
| 2014/0277033 A1 | 9/2014 | Taylor et al. |
| 2014/0288551 A1 | 9/2014 | Bharmi et al. |
| 2014/0288616 A1 | 9/2014 | Rawat et al. |
| 2014/0303617 A1 | 10/2014 | Shimada |
| 2015/0223877 A1 | 8/2015 | Behar et al. |
| 2015/0289931 A1 | 10/2015 | Puryear et al. |
| 2015/0290427 A1 | 10/2015 | Warnking |
| 2015/0335919 A1 | 11/2015 | Behar et al. |
| 2016/0000345 A1 | 1/2016 | Kobayashi et al. |
| 2016/0016016 A1 | 1/2016 | Taylor et al. |
| 2016/0045121 A1 | 2/2016 | Akingba et al. |
| 2017/0027460 A1 | 2/2017 | Shimada et al. |
| 2017/0035310 A1 | 2/2017 | Shimada et al. |
| 2017/0296264 A1 | 10/2017 | Wang |
| 2018/0022108 A1 | 1/2018 | Mori et al. |
| 2018/0042670 A1 | 2/2018 | Wang et al. |
| 2018/0064359 A1 | 3/2018 | Pranaitis |
| 2018/0078307 A1 | 3/2018 | Wang et al. |
| 2018/0185091 A1 | 7/2018 | Toth et al. |
| 2018/0221087 A1 | 8/2018 | Puryear et al. |
| 2018/0249958 A1 | 9/2018 | Toth et al. |
| 2018/0250054 A1 | 9/2018 | Gross et al. |
| 2018/0280082 A1 | 10/2018 | Puryear et al. |
| 2018/0289320 A1 | 10/2018 | Toth et al. |
| 2018/0310991 A1 | 11/2018 | Pike |
| 2018/0333204 A1 | 11/2018 | Ng |
| 2019/0046111 A1 | 2/2019 | Toth et al. |
| 2019/0046264 A1 | 2/2019 | Toth et al. |
| 2019/0076191 A1 | 3/2019 | Wang |
| 2019/0110704 A1 | 4/2019 | Wang |
| 2019/0134396 A1 | 5/2019 | Toth et al. |
| 2019/0151670 A1 | 5/2019 | Toth et al. |
| 2019/0183560 A1 | 6/2019 | Ballakur et al. |
| 2019/0307361 A1 | 10/2019 | Hettrick et al. |
| 2020/0046248 A1 | 2/2020 | Toth et al. |
| 2020/0077907 A1 | 3/2020 | Shimada et al. |

FOREIGN PATENT DOCUMENTS

| | | |
|---|---|---|
| EP | 0 767 630 B1 | 4/1997 |
| EP | 1042990 | 10/2000 |
| EP | 1 100 375 B1 | 5/2001 |
| EP | 1579889 | 9/2005 |
| EP | 1 647 305 B1 | 4/2006 |
| EP | 2 218 479 A2 | 8/2010 |
| EP | 2359764 | 8/2011 |
| EP | 2430996 | 3/2012 |
| EP | 2 457 614 A1 | 5/2012 |
| EP | 2 460 486 B1 | 6/2012 |
| EP | 2 495 012 A1 | 9/2012 |
| EP | 1503685 | 10/2012 |
| EP | 2 521 593 B1 | 11/2012 |
| EP | 2 561 903 A1 | 2/2013 |
| EP | 2 561 905 A1 | 2/2013 |
| EP | 1299035 | 2/2013 |
| EP | 2 626 022 A2 | 8/2013 |
| EP | 2 632 373 A1 | 9/2013 |
| EP | 2 662 041 A2 | 11/2013 |
| EP | 2 662 043 A2 | 11/2013 |
| EP | 2842604 | 3/2015 |
| EP | 2968984 | 8/2016 |
| EP | 2995250 | 10/2019 |
| EP | 3799931 | 4/2021 |
| GB | 2037166 | 7/1980 |
| JP | 07-178173 | 7/1995 |
| JP | 10-127678 | 5/1998 |
| JP | 11-218100 | 8/1999 |
| JP | 2002-078809 | 3/2002 |
| WO | WO 90/00420 | 1/1990 |
| WO | WO 1995/19143 | 7/1995 |
| WO | WO 98/41178 | 9/1998 |
| WO | WO 98/49957 | 11/1998 |
| WO | WO 98/52465 | 11/1998 |
| WO | WO 9902096 | 1/1999 |
| WO | WO 99/35987 | 7/1999 |
| WO | WO 99/44519 | 9/1999 |
| WO | WO 99/44523 | 9/1999 |
| WO | WO 99/52423 | 10/1999 |
| WO | WO 99/56812 | 11/1999 |
| WO | WO 00/16850 | 3/2000 |
| WO | WO 00/27292 | 5/2000 |
| WO | WO 00/42934 | 7/2000 |
| WO | WO 00/51511 | 9/2000 |
| WO | WO 00/51683 | 9/2000 |
| WO | WO 00/56237 | 9/2000 |
| WO | WO 00/67648 | 11/2000 |
| WO | WO 00/67656 | 11/2000 |
| WO | WO 00/67830 | 11/2000 |
| WO | WO 00/67832 | 11/2000 |
| WO | WO 01/80723 A2 | 11/2001 |
| WO | WO 01/82814 | 11/2001 |
| WO | WO 01/37925 | 12/2001 |
| WO | WO 01/95820 | 12/2001 |
| WO | WO 2001/37925 | 12/2001 |
| WO | WO 02/05868 | 1/2002 |
| WO | WO 02/005897 | 1/2002 |
| WO | WO 01/80723 A3 | 4/2002 |

(56) References Cited

FOREIGN PATENT DOCUMENTS

| | | |
|---|---|---|
| WO | WO 02/083196 | 10/2002 |
| WO | WO 03/003930 | 1/2003 |
| WO | WO 2003-003930 | 1/2003 |
| WO | WO 03/022167 | 3/2003 |
| WO | WO 03/051450 | 6/2003 |
| WO | WO-03/059437 A2 | 7/2003 |
| WO | WO 04/023978 | 3/2004 |
| WO | WO 2006/041881 | 4/2006 |
| WO | WO-2006/041881 A2 | 4/2006 |
| WO | WO 2006/060053 | 6/2006 |
| WO | WO 2007/014003 | 2/2007 |
| WO | WO 2011/024133 | 3/2011 |
| WO | WO 2011/051872 | 5/2011 |
| WO | WO 2011/060200 | 5/2011 |
| WO | WO 2011/060201 | 5/2011 |
| WO | WO 2011/080666 | 7/2011 |
| WO | WO 2011/101778 | 8/2011 |
| WO | WO 2012/001595 | 1/2012 |
| WO | WO 2012/025245 | 3/2012 |
| WO | WO 2012/068354 | 5/2012 |

OTHER PUBLICATIONS

Chinitz, Larry A., "Mapping Reentry Around Atriotomy Scars Using Double Potentials," 1996.
Cosio, Francisco G., "Atrial Flutter Mapping and Ablation II," Pacing & Clin. Electrophysiol. 19(6): 965-75, 1996.
Feld, Gregory K., "Radiofrequency Catheter Ablation for the Treatment of Human Type I Atrial Flutter," 1992.
Fjield, et al., U.S. Appl. No. 60/218,641, filed Jul. 13, 2000.
Gallagher, John J., "Wolff-Parkinson-White Syndrome: Surgery to Radiofrequency Catheter Ablation," 1997.
Haissaguerre, Michel, "Electrophysiological End Point for Catheter Ablation of Atrial Fibrillation Initiated From Multiple Venous Foci," 1999.
Haissaguerre, Michele, M.D., "Predominant Origin of Atrial Panarrythmic Triggers in the Pulmonary Veins: A Distinct Electrophysiologic Entity," 1997.
Haissaguerre, Michel, M.D., "Radiofrequency Catheter Ablation in Unusual Mechanisms of Atrial Fibrillation," 1994.
Haissaguerre, Michel, M.D., "Right and Left Atrial Radiofrequency Catheter Therapy of Paroxysmal Atrial Fibrillation," 1996.
Haissaguerre, Michel, M.D., "Spontaneous Initiation of Atrial Fibrillation by Ectopic Beats Originating in the Pulmonary Veins," 1998.
Hatala, Robert, "Radiofrequency Catheter Ablation of Left Atrial Tachycardia Originating Within the Pulmonary Vein in a Patient with Dextrocardia," 1996.
Hocini, Meleze, "Concealed Left Pulmonary Vein Potentials Unmasked by Left Atrial Stimulation," 2000.
Hocini, Meleze, "Multiple Sources Initating Atrial Fibrillation from a Single Pulmonary Vein Identified by a Circumferential Catheter," 2000.
Hsieh, Ming-Hsiung, M.D., "Double Multielectrode Mapping Catheters Facilitate Radiofrequency Catheter Ablation of Focal Atrial Fibrillation Originating from Pulmonary Veins," 1998.
Igawa, Osamu, "The Anatomical Features of the Junction between the Left Atrium and the Pulmonary Veins: The Relevance with Atrial Arrhythmia."
International Search Report dated Feb. 25, 2010 in Int'l PCT Patent Application Serial No. PCT/US2010/020333 (109317-2610).
Jais, Pierre, M.D., "A Focal Source of Atrial Fibrillation Treated by Discrete Radiofrequency Ablation," 1996.
Kay, G. Neal, "Radiofrequency Ablation for Treatment of Primary Atrial Tachycardia," 1993.
Krimholtz et al., "New Equivalent Circuits for Elementary Piezoelectric Transducers," Electronics Lettres, vol. 6, No. 13, pp. 398-399, Jun. 25, 1970.
Kumagai, Koichiro, "Treatment of Mixed Atrial Fibrillation and Typical Atrial Flutter by Hybrid Catheter Ablation," 2000.
Lesh, M.D., "An Anatomic Approach to Prevention of Atrial Fibrillation: Pulmonary Vein Isolation with Through-the-Balloon Ultrasound Ablation (TTB-US)," Thorac. Cardiovasc. Surg. 47 (1999) (Suppl.) 347-51.
Lesh, Michael D., M.D., "Radiofrequency Catheter Ablation of Atrial Arrhythmias," 1994.
Liem, L. Bing, "In Vitro and In Vivo Results of Transcatheter Microwave Ablation Using Forward-Firing Tip Antenna Design," 1996.
Lin, Wei-Shiang, M.D., "Pulmonary Vein Morphology in Patients with Paroxysmal Atrial Fibrillation Initiated by Ectopic Beats Originating From the Pulmonary Veins," Circulation 101(11): 1274-81, 2000.
Mallavarapu, Christopher, "Radiofrequency Catheter Ablation of Atrial Tachycardia with Unusual Left Atrial Sites of Origin," 1996.
Montenero, Sandro, Annibale, "Electrograms for Identification of the Atrial Ablation Site During Catheter Ablation of Accessory Pathways," 1996.
Moubarak, Jean B., "Pulmonary Veins-Left Atrial Junction: Anatomic and Histological Study," Pacing & Clin. Electrophys. 23(11 pt. 2): 1836-8, 2000.
O'Connor, Brian K., "Radiofrequency Ablation of a Posteroseptal Accessory Pathway Via the Middle Cardia Vein in a Six-Year Old Child," 1997.
Supplementary EP Search Report dated Sep. 16, 2005 in EP Patent Application Serial No. EP 01952750.6.
Partial EP Search Report dated Sep. 28, 2011 in EP Patent Application Serial No. 10010583.2.
Partial EP Search Report dated Sep. 26, 2011 in EP Patent Application Serial No. 10010582.4.
International Search Report dated Jan. 9, 2008 in Int'l PCT Patent Application Serial No. PCT/US07/11346.
International Search Report dated Jan. 3, 2002 in Int'l PCT Application Serial No. PCT/US2001/022221.
International Search Report dated Sep. 19, 2002 in Int'l PCT Patent Application Serial No. PCT/US01/22237.
International Search Report dated Apr. 12, 2005 in Int'l PCT Patent Application Serial No. PCT/US04/05197.
Supplementary EP Search Report dated Apr. 3, 2005 in EP Patent Application Serial No. EP 01952746.4.
Supplementary EP Search Report dated Feb. 1, 2010 in EP Patent Application Serial No. EP 07776968.
Prager, Nelson, A., "Long Term Effectiveness of Surgical Treatment of Ectopic Atrial Tachycardia," 1993.
Rappaport et al., "Wide-Aperture Microwave Catheter-Based Cardiac Ablation," Proceedings of the First Joint BMES/EMBS Conference, Oct. 13-16, 1999, p. 314.
Reuter, David, M.D., "Future Directions of Electrotherapy for Atrial Fibrillation," 1997.
Response to Written Opinion under Article 34 dated Nov. 8, 2010 in Int'l PCT Patent Application Serial No. PCT/US2010/020333.
Robbins, Ivan, M.D., "Pulmonary Vein Stenosis After Catheter Ablation of Atrial Fibrillation," 1998.
Scheinman, Melvin M., "NASPE Survey on Catheter Ablation," 1995.
Swartz, John F., "A Catheter-based Curative Approach to Atrial Fibrillation in Humans," 1994.
Swartz, John F., M.D., "Radiofrequency Endocardial Catheter Ablation of Accessory Atrioventricular Pathway Atrial Insertion Sites," 1993.
Tanaka et al., "A new radiofrequency thermal balloon catheter for pulmonary vein isolation," Journal of the American College of Cardiology 38(7): 2079-86, Dec. 2001.
Tracy, Cynthia M., "Radiofrequency Catheter Ablation of Ectopic Atrial Tachycardia Using Paced Activation Sequence Mapping," J. of Amer. College of Cardiol. 21(4): 910-7, 1993.
Van Hare, George F., "Radiofrequency Catheter Ablation of Supraventricular Arrhythmias in Patients With Congenital Heart Disease: Results and Technical Considerations," J. of the Amer. College of Cardiol. 22(3): 883-90, 1993.
Volkmer, Marius, M.D., "Focal Atrial Tachycardia from Deep Inside the Pulmonary Veins," 1997.

(56) References Cited

OTHER PUBLICATIONS

Walsh, Edward P., M.D., "Transcatheter Ablation of Ectopic Atrial Tachycardia in Young Patients Using Radiofrequency Current," 1992.
Written Opinion of the International Searching Authority dated Feb. 25, 2010 in Int'l PCT Patent Application Serial No. PCT/US2010/020333.
Zhang et al., "The development of a RF electrical pole catheter for heart ablation," China Academic Journal Electronic Publishing House 23(5): 279-80, Sep. 1999.
Zipes, Douglas P., M.D., "Catheter Ablation of Arrhythmias," 1994.
Campese, et al., Renal afferent denervation prevents hypertension in rats with chronic renal failure, Hypertension, 25:878-882 (1995).
Dibona, Renal nerves in compensatory renal response in contralateral renal denervation, Renal Physiology, 238(1):F26-F30 (1980).
Oliveira, et al., Renal Denervation Normalizes Pressure and Baroreceptor Reflext in High Renin Hypertension in Conscious Rats, Hypertension, 19:17-21 (1992).
Smithwick, R.H., Surgery in hypertension, Lancet, 2:65 (1948).
Smithwick, R.H., Surgical treatment of hypertension, Am. J. Med. 4:744-759 (1948).
Arruda, M. S., et al. "Development and validation of an ECG algorithm for identifying accessory pathway ablation site in Wolff-Parkinson-White syndrome." J Cardiovasc Electrophysiol, 9:2-12 (1998).
Avitall, B., et al. "The creation of linear continuous lesions in the atria with an expandable loop catheter." J Am Coll Cardiol, 33,4:972-984 (1999).
Bartlett, T. G., et al. "Current management of the Wolff-Parkinson-White syndrome." J Card Surg, 8:503-515 (1993).
Benito, F., et al. "Radio frequency catheter ablation of accessory pathways in infants," Heart, 78:160-162 (1997).
Blumenfeld, J. D., et al. "β-Adrenergic receptor blockade as a therapeutic approach for suppressing the renin-angiotensin-aldosterone system in norrnotensive and hypertensive subjects." AJH, 12:451-459 (1999).
Callans, D. J. "Narrowing of the superior vena cava—right atrium junction during radiofrequency catheter ablation for inappropriate sinus tachycardia: Analysis with intracardiac echocardiography." JACC, 33:1667-1670 (1999).
Cao, H., et al. "Flow effect on lesion formation in RF cardiac catheter ablation." IEEE T Bio-Med Eng, 48:425-433 (2001).
Chen, S.-A., et al. "Complications of diagnostic electrophysiologic studies and radiofrequency catheter ablation in patients with tachyarrhythmias: An eight-year survey of 3,966 consecutive procedures in a tertiary referral center." Am J Cardiol, 77 :41-46 (1996).
Cioni, R., et al. "Renal artery stenting in patients with a solitary functioning kidney." Cardiovasc Intervent Radiol, 24:372-377 (2001).
Cosby, R. L., et al. "The role of the sympathetic nervous system and vasopressin in the pathogenesis of the abnormal sodium and water." *Nefrologia*, V, 4:271-277 (1985).
Cox, J. L. "The status of surgery for cardiac arrhythmias." Circulation, 71 :413-417 (1985).
Cox, J. L., et al. "Five-year experience with the Maze procedure for atrial fibrillation." Ann Thorac Surg, 56:814-824 (1993).
Cruickshank, J. M. "Beta-blockers continue to surprise us." Eur Heart J, 21:354-364 (2000).
Curtis, J. J., et al. "Surgical therapy for persistent hypertension after renal transplantation," Transplantation, 31:125-128 (1981).
Demazumder, D., et al. "Comparison of irrigated electrode designs for radiofrequency ablation of myocardium." J Interv Card Electr, 5:391-400 (2001).
Dibona, G. F. "Neural control of the kidney: Functionally specific renal sympathetic nerve fibers." Am J Physiol Regulatory Integrative Comp Physiol, 279:R1517-R1524 (2000).
Dibona, G. F. "Sympathetic nervous system and kidney in hypertension," Nephrol and Hypertension, 11: 197-200 (2002).
Dibona, G. F., et al. "Neural control of renal function," Physiol Rev, 77:75-197 (1997).
Dibona, G. F., et al. "Renal hemodynamic effects of activation of specific renal sympathetic nerve fiber groups." Am J Physiol Regul Integr Comp Physiol, 276:R539-R549 (1999).
Doggrell, S. A., et al. "Rat models of hypertension, cardiac hypertrophy and failure." Cardiovasc Res, 39:89-105 (1998).
Dong, Q., et al. "Diagnosis of renal vascular disease with MR angiography." RadioGraphies, 19:1535-1554 (1999).
Dubuc, M., et al. "Feasibility of cardiac cryoablation using a transvenous steerable electrode catheter," J Interv Cardiac Electrophysiol, 2:285-292 (1998).
Gilard, M., et al. "Angiographic anatomy of the coronary sinus and its tributaries." PACE, 21:2280-2284 (1998).
Goriseh, W., et al. "Heat-induced contraction of blood vessels." Lasers Surg Med, 2:1-13 (1982).
Haines, D. E., et al. "Tissue heating during radiofrequeney catheter ablation; A thermodynamic model and observations in isolated perfused and superfused canine right ventricular free wall." PACE, 12:962-976 (1989).
Han, Y-M., et al. "Renal artery embolization with diluted hot contrast medium: An experimental study," J Vase Interv Radial, 12:862-868 (2001).
Hansen, J. M., et al. "The transplanted human kidney does not achieve functional reinnervation." Clin Sci, 87, 1: 13-20 (1994).
Hindricks, G. "The Multicentre European Radiofrequency Survey (MERFS): Complications of radiofrequency catheter ablation of arrhythmias." Eur Heart J, 14:1644-1653 (1993).
Ho, S. Y., et al. "Architecture of the pulmonary veins: Relevance to radiofrequency ablation." Heart, 86:265-270 (2001).
Huang et al., "Renal denervation prevents and reverses hyperinsulinemia-induced hypertension in rats," Hypertension 32, pp. 249-254 (1998).
Huang, S. K. S., et al. "Radiofrequency catheter ablation of cardiac arrhythmias: Basic concepts and clinical applications." 2nd ed. Armonk, NY: Futura Publishing Co. (2000).
Jackman, W. M., et al. "Treatment of supraventricular tachycardia due to atrioventricular nodal reentry by radiofrequency catheter ablation of slow-pathway conduction." N England J Med, 327, 5:313-318 (Jul. 30, 1992).
Jain, M. K., et al. "A three-dimensional finite element model of radiofrequency ablation with blood flow and its experimental validation." Ann Biomed Eng, 28: 1075-1084 (2000).
Janssen, B. J. A , et al. "Renal nerves in hypertension." Miner Electrolyte Metab, 15:74-82 (1989).
Kapural, L., et al. "Radiofrequency ablation for chronic pain control." Curr Pain Headache Rep, 5:517-525 (2001).
Koepke, J. P., et al. "The physiology teacher: Functions of the renal nerves." The Physiologist, 28, 1:47-52 (1985).
Kompanowska, E., et al. "Early effects of renal denervation in the anaesthetised rat: Natriuresis and increased cortical blood flow," J Physiol, 531. 2:527-534 (2001).
Labonte, S. "Numerieal model for radio-frequency ablation of the endocardium and its experimental validation." IEEE T Bio-med Eng, 41,2:108-115 (1994).
Lee, S.-J., et al. "Ultrasonic energy in endoscopic surgery," Yonsei Med J, 40:545-549 (1999).
Leertouwer, T. C., et al. "In-vitro validation, with histology, of intravascular ultrasound in renal arteries." J Hypertens, 17:271-277 (1999).
Lowe, J. E. "Surgical treatment of the Wolff-Parkinson-White syndrome and other supraventricular tachyarrhythmias." J Card Surg, 1 :117-134 (1986).
Lundin, S. et al. "Renal sympathetic activity in spontaneously hypertensive rats and normotensive controls, as studied by three different methods." Acta Physiol Scand, 120,2:265-272 (1984).
Lustgarten, D. L., et al. "Cryothermal ablation: Mechanism of tissue injury and current experience in the treatment of tachyarrhythmias," Progr Cardiovasc Dis, 41 :481-498 (1999).
McRury, I. D., et al. "Nonuniform heating during radiofrequency catheter ablation with long electrodes." Circulation, 96:4057-4064 (1997).
Mehdirad, A , et al. "Temperature controlled RF ablation in canine ventricle and coronary sinus using 7 Fr or 5 Fr ablation electrodes." PACE, 21:310-321 (1998).

(56) References Cited

OTHER PUBLICATIONS

Miller, B. F., and Keane, C. B. "Miller-Keane Encyclopedia & Dictionary 0/ Medicine, Nursing, & Allied Health." Philadelphia: Saunders (1997) ("ablation").
Misaki, T., et al. "Surgical treatment of patients with Wolff-Parkinson-White syndrome and associated Ebstein's anomaly." J Thorac Cardiovasc Surg, 110: 1702-1707 (1995).
Moak, J. P., et al. "Case report: Pulmonary vein stenosis following RF ablation of paroxysmal atrial fibrillation: Successful treatment with balloon dilation." J Interv Card Electrophys, 4:621-631 (2000).
Morrissey, D. M., "Sympathectomy in the treatment of hypertension." Lancet, CCLXIV:403-408 (1953).
Nakagawa, H., et al. "Comparison of in vivo tissue temperature profile and lesion geometry for radiofrequeney ablation with a saline-irrigated electrode versus temperature control in a eanine thigh muscle preparation." Circulation, 91 :2264-2273 (1995).
Nakagawa, H., et al. "Inverse relationship between electrode size and lesion size during radiofrequency ablation with active electrode cooling." Circulation, 98:458-465 (1998).
Nakagawa, A , et al. "Selective ablation of porcine and rabbit liver tissue using radiofrequency: Preclinical study." Eur Surg Res, 31: 3 71-379 (1999).
Neutel, J. M. "Hypertension and its management: A problem in need of new treatment strategies." JRAAS, I:S 1 0-S 13 (2000).
Nozawa, T., et al. "Effects of long-term renal sympathetic denervation on heart failure after myocardial infarction in rats." Heart Vessels, 16:51-56 (2002).
Oliveira et al., "Renal Denervation Normalizes Pressure and Baroreceptor Reflex in High Renin Hypertension in Conscious Rats," Hypertension Suppl. II vol. 19 No. 2, pp. 17-21 (1992).
Oral, H., et al. "Pulmonary vein isolation for paroxysmal and persistent atrial fibrillation." Circulation, 105: 1 077-1081 (2002).
Page, I., et al. "The effect of renal denervation on the level of arterial blood pressure and renal function in essential hypertension." J Clin Invest, XIV:27-30 (1935).
Panescu, D., et al. "Radiofrequency multielectrode catheter ablation in the atrium." Phys Med Biol, 44:899-915 (1999).
Pavin, D., et al. "Permanent left atrial tachyeardia: Radiofrequency catheter ablation through the eoronary sinus." J Cardiovasc Electrophysiol, 12:395-398 (2002).
Peet, M., "Hypertension and its surgical treatment by bilateral supradiaphragmatic splanchnicectomy," Am. J. Surgery, pp. 48-68 (1948).
Petersen, H. H., et al. "Lesion dimensions during temperature controlled radiofrequency catheter ablation of left ventricular porcine myocardium: Impact of ablation site, electrode size, and convective cooling." Circulation, 99:319-325 (1999).
Pohl, M.A. "Renovaseular hypertension and isehemie nephropathy" A chapter in a book edited by Sehrier, R. W. "Atlas of diseases of the kidney: Hypertension and the kidney." Blackwell Scienee (1999).
Pugsley, M. K., et al. "The vascular system: An overview of structure and function." J Pharmacol Toxical Methods, 44:333-340 (2000).
Sanderson, J. E., et al. "Effect of B-blockage on baroreceptor and autonomic function in heart failure." Clin Sei, 69:137-146 (1999).
Schauerte, P., et al. "Catheter ablation of cardiac autonomic nerves for prevention of vagal atrial fibrillation," Circulation, 102:2774-2780 (2000).
Scheinman, M. M., et al. "The 1998 NASPE prospective catheter ablation registry." PACE, 23:1020-1028 (2000).
Smithwick et al., "Splanchnicectomy for Essential Hypertension," J. Am. Med. Assn. 152:16, pp. 1501-1504 (1953).
Solis-Herruzo et al., "Effects of Lumbar Sympathetic Block on Kidney Function in Cirrhotic Patients with Hepatorenal Syndrome," J. Hepatol. 5, pp. 167-173 (1987).
Stella, A , et al. "Effects of reversible renal denervation on haemodynamic and excretory functions of the ipsilateral and contralateral kidney in the cat," J Hypertension, 4: 181-188 (1986).
Stellbrink, C., et al. "Transcoronary venous radiofrequency catheter ablation of ventricular tachyeardia." J Cardiovasc Electrophysiol, 8:916-921 (1997).
Swain, et al. Gastrointestinal Endoscopy. 1994; 40:AB35.
Takahashi, H., et al. "Retardation of the development of hypertension in DOCA-salt rats by renal denervation." Jpn Circ J, 48:567-574 (1984).
Tungjitkusolmun, S. "Ablation." A chapter in a book edited by Webster, J. G., "Minimally invasive medical technology." Bristol UK: IOP Publishing, 219 (2001).
Uchida, F., et al. "Effect of radio frequency catheter ablation on parasympathetic denervation: A comparison of three different ablation sites," PACE, 21:2517-2521 (1998).
Uflacker, R., "Atlas of vascular anatomy: An angiographic approach." Baltimore: Williams & Wilkins, 424 (1997).
Valente, J. F. "Laparoscopic renal denervation for intractable ADPKD-related pain," Nephrol Dial Transplant, 16:160 (2001).
Van Hare, G. F., et al. "Percutaneous radiofrequency catheter ablation for supraventricular arrhythmias in children." JACC, 17:1613-1620 (1991).
Vujaskovie, Z., et al. "Effects of intraoperative hyperthermia on canine seiatie nerve: Histopathologie and morphometric studies." Int J Hyperthermia, 10,6:845-855 (1994).
Weinstock, M., et al. "Renal denervation prevents sodium retention and hypertension in salt-sensitive rabbits with genetic baroreflex impairment," Clinical Science, 90:287-293 (1996).
Weir, M. R., et al. "The renin-angiotensin-aldosterone system: A specific target for hypertension management." Am J Hypertens, 12:205S-213S (1999).
Yamamoto, T., et al. "Blood velocity profiles in the human renal artery by Doppler ultrasound and their relationship to atherosclerosis." Arterioscl Throm Vas, 16: 172-177 (1996).
Extended EP Search Report dated Jul. 12, 2012 in EP Patent Application Serial No. EP 10729496.9.
Supplementary EP Search Report dated Dec. 13, 2005 in EP Patent Application Serial No. EP 01952750.6.
Accornero, Neri, et al., "Selective Activation of Peripheral Nerve Fibre Groups of Different Diameter by Triangular Shaped Stimulus Pulses", J. Physiol. (1977), 273, _ 539-560, 22 Q9S.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 758-765 (2012).
American Heart Association—Pulmonary Hypertension: High Blood Pressure in the Heart-to-Lung System, (last reviewed Oct. 31, 2016).
Appeal Brief of Patent Owner from Reexamination 95-002,110.
Aytac, et al., "Correlation Between the Diameter of the Main Renal Artery and the Presence of an Accessory Renal Artery", J Ultrasound Med 22:433-439, 2003.
Azizi, Michel et al., Ultrasound renal denervation for hypertension resistant to a triple medication pill (Radiance-HTN Trio): a randomised, multicentre, single-blind, sham-controlled trial, 397 Lancet 2476 (2021).
Bailey, M.R. et al., Physical Mechanisms of the Therapeutic Effect of Ultrasound (a Review), Acoustical Physics, vol. 49, No. 4, 2003, pp. 369-388.
Bengel, et al., Serial Assessment of Sympathetic Reinnervation After Orthotopic Heart Transplantation; A Longitudinal Study Using PET and C-11 Hydroxyephedrine, Circulation. 1999;99: 1866-1871.
Bhatt, D.L., et al., A Controlled Trial of Renal Denervation for Resistant Hypertension, New England J. Med., 370:1393-1401 (2014).
Bhatt, Deepak L. et al., Long-term outcomes after catheter-based renal artery denervation for resistant hypertension: final follow-up of the randomised Symplicity HTN-3 Trial, 400 Lancet 1405 (2022).
Bisdas, Theodosios et al., Initial Experience with the 6-F and 8-F Indigo Thrombectomy System for Acute Renovisceral Occlusive Events, Journal of Endovascular Therapy, vol. 24, No. 4, 604-610 (2017).

(56) References Cited

OTHER PUBLICATIONS

Blanketjin, Peter, Sympathetic Hyperactivity in Chronic Kidney Disease, Neprhrol Dial Transplant, vol. 19, No. 6, 1354-1357 (2004).
Blum et al., Treatment of Ostial Renal-Artery Stenoses with Vascular Endoprostheses after Unsuccessful Balloon Angioplasty, N. Engl. J. Med. 336 459-65 (1997).
Bonsignore, C., "A Decade of Evolution in Stent Design", Proceedings of the International Conference on Shape Memory and Superelastic Technologies, (2003).
Bradfield, Jason S. et al., Renal denervation as adjunctive therapy to cardiac sympathetic denervation for ablation refractory ventricular tachycardia, Heart Rhythm Society, vol. 17, No. 2, 220-227 (2020).
Bush, et al., "Endovascular revascularization of renal artery stenosis: Technical and clinical results", Journal of Vascular Surgery, May 2001, 1041-1049 (2001).
Camasao, D.B. et al., The mechanical characterization of blood vessels and their substitutes in the continuous quest for physiological-relevant performances: A critical review, Materials Today Bio, vol. 10 (2021).
Carter, J., "Microneurography and Sympathetic Nerve Activity: A Decade-By-Decade Journey across 50 Years," Journal of Neurophysiology, vol. 121, No. 4. doi: 10.1 152/jn.00570.2018.
Carter, Stefan et al., Measurement of Renal Artery Pressures by Catheterization in Patients with and without Renal Artery Stenosis, Circulation, vol. XXXIII, 443-449 (1966).
Charlesworth, Peter et al., Renal Artery Injury From a Fogarty Balloon Catheter, Journal of Vascular Surgery, vol. 1, No. 4, 573-576 (1984).
Chart showing priority claims of the '629 patent, exhibit to Petition for Inter Partes Review of U.S. Pat. No. 8,845,629, filed Jan. 13, 2022 in the Patent Trial and Appeal Board, United States Patent and Trademark Office, Petition No. PTAB-IPR2022-00431.
Chiesa et al., Endovascular Stenting for the Nutcracker Phenomenon, J. Endovasc. Ther., 8:652-655 (2001).
Corrected Patent Owner's Response to Office Action, dated May 10, 2013, from File History of Inter Partes Reexamination 95/002,110.
Correspondence from PTAB Deputy Chief Clerk to Counsel re conference call request-Exhibit 3001 in the Patent Trial and Appeal Board, United States Patent and Trademark Office, Petition No. PTAB-IPR2022-00431.
Curriculum Vitae of Dr. John M. Moriarty.
Curriculum Vitae of Dr. Michael Bohm.
Curriculum Vitae of Farrell Mendelsohn.
Curriculum Vitae of Dr. Chris Daft.
Dangas, G., et al., Intravascular Ultrasound-Guided Renal Artery Stenting, J Endovasc Ther, 2001;8:238-247 (2001).
Deardorff, Dana et al., Ultrasound Applicators with Internal Water-Cooling for High-Powered Interstitial Thermal Therapy, IEEE Transactions on Biomedical Engineering, vol. 47, No. 10, 1356-1365 (2000).
Decision of the Patent Trial and Appeal Board in U.S. Appl. No. 14/731,347.
Declaration of Chris Daft dated Jan. 11, 2022, in the Patent Trial and Appeal Board, United States Patent and Trademark Office, Petition No. PTAB-IPR2022-00431.
Second Declaration of Chris Daft. Dated Jan. 10, 2023, in the Patent Trial and Appeal Board, United States Patent and Trademark Office, Petition No. PTAB-IPR2022-00431.
Declaration of Dr. Daniel van der Weide, dated Oct. 26, 2022, in the Patent Trial and Appeal Board, United States Patent and Trademark Office, Petition No. PTAB-IPR2022-00431.
Declaration of Dr. Dieter Haemmerich, dated Aug. 29, 2012, in the Patent Trial and Appeal Board, United States Patent and Trademark Office, In re U.S. Pat. No. 7,717,948.
Declaration of Dr. John M. Moriarty in German Nullity proceedings for EP 2261905, dated Jul. 13, 2022.
Declaration of Dr. John Moriarty, dated Jan. 19, 2023, in the Patent Trial and Appeal Board, United States Patent and Trademark Office, Petition No. PTAB-IPR2022-00431.

Declaration of Jonathan Bradford in Support of Patent Owner'sResponse, dated Oct. 27, 2022.
Declaration of Jonathan Bradford dated May 10, 2022, in the Patent Trial and Appeal Board, United States Patent and Trademark Office, Petition No. PTAB-IPR2022-00431.
Declaration of Dr. Michael Bohm dated Sep. 29, 2022 on behalf of Medtronic Inc.
Declaration of Dr. Robert Tucker, dated Oct. 27, 2022, in the Patent Trial and Appeal Board, United States Patent and Trademark Office, Petition No. PTAB-IPR2022-00431.
Declaration of Farrell Mendelsohn dated Jan. 10, 2022, in the Patent Trial and Appeal Board, United States Patent and Trademark Office, Petition No. PTAB-IPR2022-00431.
Defendant's Reply to Court Order of Oct. 4, 2022 and Plaintiff's Surrejoinder of Sep. 29, 2022 in the Mannheim District Court, case No. 7 O 14/21, dated Oct. 31, 2022.
Defendant's Response dated May 11, 2022 in the Munich Federal Patent Court, Nullity Suit 6 Ni 32/22.
Diederich, et al., Ultrasound Catheters for Circumferential Cardiac Ablation, in Proceedings of SPIE Conference on Thermal Treatment of Tissue with Image Guidance San Jose, California, Jan. 1999 SPIE vol. 3594.
Diedrich, A. et al.,"Analysis of Raw Microneurographic Recordings Based on Wavelet De-Noising Technique and 1 Classification Algorithm: Wavelet Analysis in Microneurography," IEEE Trans Biomed Eng. Jan. 2003 ; 50(1): 41-50_ doi:10.1109fTBME.2002. 807323.
Draney, Mary et al., Three-Dimensional Analysis of Renal Artery Bending Motion During Respiration, International Society of Endovascular Specialists, vol. 12, 380-386 (2005).
EP Board of Appeals Communication dated Dec. 17, 2019—Preliminary Remarks for EP appeal No. T2680/16-3.3.4.01.
Erikson, Kenneth et al., Ultrasound in Medicine: A Review, IEEE Transactions on Sonics and Ultrasonics, vol. 21, No. 3 (1974).
European Communication dated Oct. 23, 2013 in EP Application No. 12180431.4.
European Office Action re Application No. 12180431.4.
European Patent No. 12167931, Claims of the Main Request dated Sep. 30, 2016.
European Search Report (supplementary) dated Feb. 17, 2016 in European Patent Application No. 14775754.6.
European Search Report dated Mar. 1, 2021 in European Patent Application No. 20202272.9.
European Search Report for Patent Application No. EP12180431 dated Jan. 17, 2013.
Fengler, Karl et al., A Three-Arm Randomized Trial of Different Renal Denervation Devices and Techniques in Patients With Resistant Hypertension (Radiosound-HTN), 139 Circulation 590 (2019).
File History to EP1802370B1 Part 1.
File History to EP1802370B1 Part 2.
File History to EP1802370B1 Part 3.
Gallitto, Enrico et al., Renal Artery Orientation Influences the Renal Outcome in Endovascular Thoraco-abdominal Aortic Aneurysm Repair, European Society of Endovascular Surgery, vol. 56, No. 3, 382-390 (2018).
Gervais, Debra A. et al., Radiofrequency ablation of renal cell carcinoma: Part 2, Lessons learned with ablation of 100 tumors, 185 AJR Am. J. Roentgenol. 72 (2005).
Goldberg, S. Nahum et al., EUS-guided radiofrequency ablation in the pancreas: results in a porcine model, 50 Gastrointest. Endosc. 392 (1999).
Golwyn et al., Percutaneous Transcatheter Renal Ablation with Absolute Ethanol for Uncontrolled Hypertension or Nephrotic Syndrome: Results in 11 Patients with End-Stage Renal Disease, J. Vasco and Interventional Radiology, 8,527-433 (1997).
Gorsich, W., et al., Heat-Induced Contraction of Blood Vessels, Lasers in Surgery and Medicine, 2:1-13 (1982).
Gray, Henry, Gray's Anatomy: The Anatomical Basis of Medicine and Surgery, Churchill Livingstone, New York, NY (1995).
Habict, Antje et al., Sympathetic Overactivity and Kidneys, The Middle European Journal of Medicine, vol. 115, 634-640 (2003).

(56) References Cited

OTHER PUBLICATIONS

Harrison, R.R. et al., "A Low-Power Integrated Circuit for a Wireless 1 OD-Electrode Neural Recording System," IEEE Journal of Solid-State Circuits, vol. 42, No. 1, pp. 123-133, Jan. 2007. doi: 10.1 109/JSSC.2006.886567.
He, D. S. et al., Application of Ultrasound Energy for Intracardiac Ablation of Arrhythmias, European Heart Journal, vol. 16, 961-966 (1995).
Heffner, H. et al., "Gain, Band Width, and Noise Characteristics of the Variable-Parameter Amplifier," Journal of Applied Physics, vol. 29, No. 9, Sep. 1 958, 1 1 pages.
Holmes, David R. et al., Pulmonary vein stenosis complicating ablation for atrial fibrillation: clinical spectrum and interventional considerations, 2 JACC Cardiovasc. Interv. 267 (2009).
Hsu, Thomas H. S. et al., Radiofrequency ablation of the kidney: acute and chronic histology in porcine model, 56 Urology 872 (2000).
Institution Decision Granting Institution of Inter Partes Review 35 U.S.C. sec. 314, dated Aug. 8, 2022 in the Patent Trial and Appeal Board, United States Patent and Trademark Office, Petition No. PTAB-IPR2022-00431.
Isles et al., Management of Renovascular Disease: A Review of Renal Artery Stenting in Ten Studies, QJM 92, 159-67 (1999).
Ivanisevic, N., "Circuit Design Techniques for Implantable Closed-Loop Neural Interfaces," Doctoral Thesis in Information and Communication Technology, KTH School of Electrical Engineering and Computer Science, Sweden, May 2019, 92 pages.
Janzen, Nicolette et al., Minimally Invasive Ablative Approaches in the Treatment of Renal Cell Carcinoma, Current Urology Reports, vol. 3 (2002).
Kaltenbach, Benjamin et al., Renal Artery Stenosis After Renal Sympathetic Denervation, Journal of the American College of Cardiology, vol. 60, No. 25 (2012).
Katholi, R.E., et al., Importance of Renal Sympathetic Tone in the Development of DOCA-Salt Hypertension in the Rat, Hypertension, 2:266-273 (1980).
Kim, Yun-Hyeon et al., Pulmonary vein diameter, cross-sectional area, and shape: CT analysis, Radiology Society of North America, vol. 235, No. 1, 49-50 (2005).
Kirsh, Danielle, Balloon Catheters: What are some key design considerations?, Massdevice (Dec. 6, 2016).
Koomans, Hein et al., Sympathetic Hyperactivity in Chronic Renal Failure: A wake-up call, Frontiers in Nephrology, vol. 15, 524-537 (2004).
Kuo, et al., "Atrial Fibrillation: New Horizons", Chang Gung Med J vol. 26 No. 10 Oct. 2003.
Lang, Roberto et al., Recommendations for Chamber Quantification: A Report from the American Society of Echocardiography's Guidelines and Standards Committee and the Chamber Quantification Writing Group, Developed in Conjunction with the European Association of Echocardiography, a Branch of the European Society of Cardiology, Journal of the American Society of Echocardiography, vol. 18, No. 12, 1440-1463 (2005).
Lee, Jong Deok et al., MR imaging-histopathologic correlation of radiofrequency thermal ablation lesion in a rabbit liver model: observation during acute and chronic stages, 2 Korean J. Radiol. 151 (2001).
Levin, S., et al., ARDIAN: Succeeding Where Drugs Fail—Treating Hypertension in the Cath Lab, In Vivo, 27:23 (2009).
Mahfoud, Felix et al., Catheter-Based Renal Denervation Is No Simple Matter: Lessons to Be Learned From Our Anatomy?, Journal of the American College of Cardiology, vol. 64, No. 7, 644-647 (2014).
Marine, Joseph E., Catheter ablation therapy for supraventricular arrhythmias, 298 JAMA 2768 (2007).
Martin, Louis K. et al., Long-term Results of Angioplasty in 110 Patients with Renal Artery Stenosis, Journal of Vascular and Interventional Radiology, vol. 3, No. 4, 619-626 (1992).

Maslov, P., "Recruitment Pattern of Muscle Sympathetic Nerve Activity in Chronic Stable Heart Failure Patients and in Healthy Control Subjects," Doctoral Dissertation, University of Split, Croatia, 2013, 69 pages.
Matsumoto, Edward D. et al., Short-term efficacy of temperature-based radiofrequency ablation of small renal tumors, 65 Urology 877 (2005).
Medtronic Press Release, Medtronic Announces U.S. Renal Denervation Pivotal Trial Fails to Meet Primary Efficacy Endpoint While Meeting Primary Safety Endpoint (Jan. 9, 2014).
Medtronic Inc., Renal Denervation (RDN): Novel Catheter-Based Treatment for Hypertension, Scientific Background, 2011.
Medtronic Scientific Background, Hypertension and the Symplicity Renal Denervation System.
Medtronic, Symplicity RDN Common System Q&A.
Medtronic Inc., The Symplicity RDN System, 2012.
Meyers, Philip et al., Temporary Endovascular Balloon Occlusion of the Internal Carotid Artery with a Nondetachable Silicone Balloon Catheter: Analysis Technique and Cost, American Journal of Neuroradiology, vol. 20, No. 4, 559-564 (1999).
Millard, et al., Renal Embolization for Ablation of Function in Renal Failure and Hypertension, Postgraduate Med. J. 65, 729-734 (1989).
Mitchell, et al., "The Renal Nerves" British Journal of Urology, Read by invitation at the Sixth Annual Meeting of the British Association of Urological Surgeons on Jun. 30, 1950.
Nair et al., "The Need for and the Challenges of Measuring Renal Sympathetic Nerve Activity," Heart Rhythm 2016; 13:1166-1171.
Natale, Andrea et al., First Human Experience with Pulmonary Vein Isolation Using a Through-the-Balloon Circumferential Ultrasound Ablation System for Recurrent Atrial Fibrillation, Circulation, vol. 102, 1879-1882 (2000).
Netter, Frank, Atlas of Human Anatomy, Icon Learning Systems, Rochester, NY (2002).
Neumann, Jutta, Sympathetic hyperactivity in chronic kidney disease: Pathogenesis, clinical relevance, and treatment, International Society of Nephrology, vol. 65, 1568-1576 (2004).
News, Columbia University Irving Medical Center, Zapping Nerves with Ultrasound Lowers Drug-Resistant Blood Pressure (May 16, 2021), https://www.cuimc.columbia.edu/news/zapping-nervesultrasound-lowers-drug-resistant-blood-pressure.
Notice of Deposition of Tucker, filed Dec. 30, 2022 in the Patent Trial and Appeal Board, United States Patent and Trademark Office, Petition No. PTAB-IPR2022-00431.
Notice of Deposition of van der Weide, filed Dec. 30, 2022 in the Patent Trial and Appeal Board, United States Patent and Trademark Office, Petition No. PTAB-IPR2022-00431.
Notice re filing date accorded, dated Feb. 10, 2022 in the Patent Trial and Appeal Board, United States Patent and Trademark Office, Petition No. PTAB-IPR2022-00431.
Order: Conduct of the Proceeding Scheduling Order 37 C.F.R. sec. 42.5, dated Aug. 8, 2022 in the Patent Trial and Appeal Board, United States Patent and Trademark Office, Petition No. PTAB-IPR2022-00431.
Olsson, R. et al., "A Three-Dimensional Neural Recording Microsystem With Implantable Data Compression 5 Circuitry," ISSCC. 2005 IEEE International Digest of Technical Papers. Solid-State Circuits Conference, 2005., San Francisco, CA, 2005, pp. 558-559 vol. 1 doi:10.1109/JSSC.2005.858479.
Order Setting Oral Hearing 37 C.F.R. § 42.70, dated Mar. 24, 2023 in the Patent Trial and Appeal Board, United States Patent and Trademark Office, Petition No. PTAB-IPR2022-00431.
Osborn, J., "Catheter-Based Renal Nerve Ablation as a Novel Hypertension Therapy, Lost, and Then Found," in Translation.
Page, Irvine H. & George J. Heuer, The Effect of Renal Denervation on Patients Suffering from Nephritis, 14 J. Clinical Investigation 443 (1935).
Papademetriou, Vasilios et al., Renal Sympathetic Denervation for the Treatment of Difficult-to-Control or Resistant Hypertension, 2011 Int. J. Hypertension, Article 196518 (2011).
Papademetriou, et al., "Renal Sympathetic Denervation: Hibernation or Resurrection?", Cardiology 2016 ; 135, 11 pgs.

(56) References Cited

OTHER PUBLICATIONS

Pappone C, et al., "Circumferential radiofrequency ablation of pulmonary vein ostia: a new anatomic approach for curing atrial fibrillation", Circulation. 2000; 102(21): 2619-2628. (2000).
Patent Owner's Amended Objections to Evidence Under 37 C.F.R. §42.64.
Patent Owner's Mandatory Notice, filed Feb. 3, 2022 in the Patent Trial and Appeal Board, United States Patent and Trademark Office, Petition No. PTAB-IPR2022-00431.
Patent Owner's Notice of Deposition of Dr. Chris Daft, filed Sep. 20, 2022 in the Patent Trial and Appeal Board, United States Patent and Trademark Office, Petition No. PTAB-IPR2022-00431.
Patent Owner's Notice of Deposition of Dr. Chris Daft filed Feb. 21, 2023 in the Patent Trial and Appeal Board, United States Patent and Trademark Office, Petition No. PTAB-IPR2022-00431.
Patent Owner's Notice of Deposition of Dr. Farrell Mendelsohn, filed Sep. 21, 2022 in the Patent Trial and Appeal Board, United States Patent and Trademark Office, Petition No. PTAB-IPR2022-00431.
Patent Owner's Notice of Deposition of Dr. John Moriarty, filed Feb. 21, 2023 in the Patent Trial and Appeal Board, United States Patent and Trademark Office, Petition No. PTAB-IPR2022-00431.
Patent Owner's Objections to Evidence, filed Aug. 18, 2022 in the Patent Trial and Appeal Board, United States Patent and Trademark Office, Petition No. PTAB-IPR2022-00431.
Patent Owner's Power of Attorney, filed Feb. 3, 2022 in the Patent Trial and Appeal Board, United States Patent and Trademark Office, Petition No. PTAB-IPR2022-00431.
Patent Owner Medtronic Ireland Power of Attorney, filed May 10, 2022 in the Patent Trial and Appeal Board, United States Patent and Trademark Office, Petition No. PTAB-IPR2022-00431.
Patent Owner's Preliminary Response, filed May 10, 2022 in the Patent Trial and Appeal Board, United States Patent and Trademark Office, Petition No. PTAB-IPR2022-00431.
Patent Owner's Request for Oral Hearing, filed Mar. 23, 2023 in the Patent Trial and Appeal Board, United States Patent and Trademark Office, Petition No. PTAB-IPR2022-00431.
Patent Owner's Response, filed Oct. 27, 2022 in the Patent Trial and Appeal Board, United States Patent and Trademark Office, Petition No. PTAB-IPR2022-00431.
Patent Owner's Sur-Reply, filed Mar. 9, 2023 in the Patent Trial and Appeal Board, United States Patent and Trademark Office, Petition No. PTAB-IPR2022-00431.
Patent Owner's Updated Mandatory Notice, filed May 10, 2022 in the Patent Trial and Appeal Board, United States Patent and Trademark Office, Petition No. PTAB-IPR2022-00431.
Petition for Inter Partes Review of U.S. Pat. No. 8,845,629, dated Jan. 13, 2022 by ReCor Medical, Inc. and Otsuka Medical Devices Co., Ltd., in the Patent Trial and Appeal Board, United States Patent and Trademark Office, Petition No. PTAB-IPR2022-00431.
Petitioner ReCor's Biography of Dr. Neil C. Barman.
Petitioner's Power of Attorney for Otsuka Medical Devices Co., Ltd., filed Jan. 13, 2022 in the Patent Trial and Appeal Board, United States Patent and Trademark Office, Petition No. PTAB-IPR2022-00431.
Petitioner's Power of Attorney for Recor Medical, Inc., filed Jan. 13, 2022 in the Patent Trial and Appeal Board, United States Patent and Trademark Office, Petition No. PTAB-IPR2022-00431.
Petitioner Reply, filed Jan. 23, 2023 in the Patent Trial and Appeal Board, United States Patent and Trademark Office, Petition No. PTAB-IPR2022-00431.
Petitioners' Request for Oral Argument, filed Mar. 21, 2023 in the Patent Trial and Appeal Board, United States Patent and Trademark Office, Petition No. PTAB-IPR2022-00431.
Petitioners' Updated Mandatory Notices, dated Jan. 18, 2022 in the Patent Trial and Appeal Board, United States Patent and Trademark Office, Petition No. PTAB-IPR2022-00431.
Plaintiff's Nullity Brief, dated Jan. 14, 2022, in the Munich Federal Patent Court, Nullity Suit 6 Ni 32/22.

Plaintiff's Reply to the May 11, 2022 Response, dated Jul. 18, 2022, in the Munich Federal Patent Court, Nullity Suit 6 Ni 32/22.
Plaintiff's Response to Court Order disagreeing with Stay of Proceedings dated Oct. 28, 2022 in Mannheim District Court, Infringement suit 7 O 147/21.
Plaintiff's Technical Brief dated Sep. 29, 2022 in the Mannheim District Court, Infringement suit 7 O 147/21.
Plouin et al., Blood Pressure Outcome of Angioplasty in Atherosclerotic Renal Artery Stenosis: A Randomized Trial. Essai Multicentrique Medicaments vs Angioplastie (EMMA) Study Group, Hypertension 31, 823-29 (1998).
Prochnau, Dirk et al., Catheter-based renal denervation for drug-resistant hypertension by using a standard electrophysiology catheter, EuroIntervention, vol. 7, 1077-1080 (2012).
Pugsley, et al., The vascular system: An overview of structure and function, Journal of Pharmacological and Toxicological Methods 44 (2000) 333-340.
Pürerfellner, Helmut et al., Incidence, Management and Outcome in Significant Pulmonary Vein Stenosis Complicating Ablation for Atrial Fibrillation, 93 Am. J. Cardiol. 1428 (2004).
Pürerfellner, Helmut & Martin Martinek, Pulmonary vein stenosis following catheter ablation of atrial fibrillation, 20 Curr. Opin. Cardiol. 484 (2005).
Reaz, M.B.I., et al., "Techniques of EMG signal analysis: detection, processing, classification and applications," Biological Procedures Online, Jan. 2006, 25 pages.
Romanes, G.J., Cunningham's Textbook of Anatomy (11th ed. 1972).
Ryan, Thomas et al., Proceedings of Thermal Treatment of Tissue with Image Guidance, Progress in Biomedical Optics, vol. 3594 (1999).
Ryan, Thomas P._ Thermal Treatment of Tissue with Image Guidance; Ultrasound Catheters for Circumferential Cardiac Ablation 1999.
Ryan, Steve, What are the Risks Associated with a Pulmonary Vein Ablation Procedure?, Atrial Fibrillation: Resources for Patients (last accessed Oct. 18, 2022).
Sakakura, Kenichi et al., Anatomic Assessment of Sympathetic Peri-Arterial Renal Nerves in Man, Journal of the American College of Cardiology, vol. 64, No. 7, 635-643 (2014).
Salmanpour, A., L. J. Brown and J. K. Shoemaker, "Detection of Single Action Potential in Multi-Unit Postganglionic 7 Sympathetic Nerve Recordings in Humans: A Matched Wavelet Approach," 2010 IEEE International Conference on Acoustics, Speech and Signal Processing, Dallas, TX, 2010, pp. 554-557. doi: 10.1 109/ICASSP. 2010.5495604.
Sánchez-Quintana, Damian et al., How close are the phrenic nerves to cardiac structures? Implications for cardiac interventionalists, 16 J. Cardiovasc. Electrophysiol 309 (2005) ("Sánchez-Quintana").
Schlaich, M.P. et al., "Renal Denervation: A Potential New Treatment Modality for Polycystic Ovary Syndrome," Journal of Hypertension, vol. 29, No. 5, pp. 991-996 201 1 . doi:10.1097/HJH. 0b013e328344db3a.
Schmieder, Ronald E., Renal denervation in patients with chronic kidney disease: current evidence and future perspectives, Nephrol. Dial. Transplant. gfac189 (2022).
Schmidt, Boris, et al., "Pulmonary Vein Isolation by High Intensity Focused Ultrasound," Indian Pacing and Electrophysiology Journal, pp. 126-133 (2006).
Schneider, Peter, Endovascular Skills: Guidewire and Catheter Skills for Endovascular Surgery, 2nd ed., Marcel Dekker, Inc., New York, NY (2003).
Schneider, Peter A., Endovascular Skills, Quality Medical Publishing, Inc., 1998 ("Schneider").
Selected documents from the File History of Inter Partes Reexamination 95/002110, exhibit to Petition for Inter Partes Review of U.S. Pat. No. 8,845,629, filed Jan. 13, 2022 in the Patent Trial and Appeal Board, United States Patent and Trademark Office, Petition No. PTAB-IPR2022-00431.
Shimizu, Kazumasa et al., Sympathetic Dysfunction in Heart Failure, Bailliere's Clinical Endocrinology and Metabolism, vol. 7, No. 2 (1993).

(56) References Cited

OTHER PUBLICATIONS

Shonai et al., Renal Artery Aneurysm: Evaluation with Color Doppler Ultrasonography Before and lifter Percutaneous Transarterial Embolization, J. Ultrasound Med. 19, 277-80 (2000)("Shonai 2000").
Slide deck from Medtronic Circulatory System Devices Panel Meeting, General Issues Panel: Clinical Evaluation of Anti-Hyperintensive Devices (Dec. 5, 2018).
Smithwick, R. H., et al., "Splanchnicectomy for essential hypertension." J. Am. Med. Assoc., 152:1501-1504 (1953).
Stipulation Modifying Schedule, dated Dec. 30, 2022 in the Patent Trial and Appeal Board, United States Patent and Trademark Office, Petition No. PTAB-IPR2022-00431.
Stipulation Modifying Schedule, dated Feb. 16, 2023 in the Patent Trial and Appeal Board, United States Patent and Trademark Office, Petition No. PTAB-IPR2022-00431.
Stoeckel, D. et al., A Survey of Stent Designs, Min Invas Ther & Allied Technol 2002: 11(4) 137-147 (2002).
Swartz, John F. et al., Radiofrequency Endocardial Catheter Ablation of Accessory Atrioventricular Pathway Atrial Insertion Sites, 87 Circulation 487 (1993).
Tank, J. et al., "Spike Rate of Multi-Unit Muscle Sympathetic Nerve Fibers Following Catheter-Based Renal Nerve Ablation," J Am. Soc Hypertens, Oct. 2015 ; 9(10): 794-801 . doi:10.1016/j.jash.2015. 07.012.
Teigen et al., Segmental Renal Artery Embolization for Treatment of Pediatric Renovascular Hypertension, J. Vasco Interv. Radiol. 3, 111-7 (1992).
Thatipelli, Mallik R., et al., CT angiography of renal artery anatomy for evaluating embolic protection devices, 18 J. Vasc. Interv. Radiol. 842 (2007).
The Doctors and Experts at WebMD, Webster's New World Medical Dictionary (3rd ed. 2008) ("WebsterMD").
Transcript of the Mar. 2, 2023 deposition of Dr. John Moriarty.
Transcript of the Mar. 3, 2023 deposition of Dr. Chris Daft.
Transcript of deposition of the Jan. 1, 2023 deposition of Dr. Robert Tucker.
Transcript of the Jan. 14, 2023 deposition of Dr. Daniel van der Weide.
Transcript of the Sep. 30, 2022 deposition of Dr. Chris Daft.
Transcript of the Oct. 1, 2022 deposition of Dr. Farrell Mendelsohn.
Tsao, Hsuan-Ming et al., Evaluation of Pulmonary Vein Stenosis after Catheter Ablation of Atrial Fibrillation, 6 Card. Electrophysiol. Rev. 397 (2002).
Turner, et al., "Initial Experience Using the Palmaz Corinthian Stent for Right Ventricular Outflow Obstruction in Infants and Small Children", Catheterization and Cardiovascular Interventions 51:444-449 (2000).
Vaezy, Shahram et al., Image-Guided Acoustic Therapy, Annual Review Biomedical Engineering, vol. 3, 375-390 (2001).
Vujaskovic, Z. et al., (1994) Effects of intraoperative hyperthermia on canine sciatic nerve: histopathologic and morphometric studies, International Journal of Hyperthermia, 10:6, 845-855 (1994) ("Vujaskovic 1994").
Wanchoo, Nishey, Medtronic Gets European and Australian Approval for Symplicity Spyral Multi-Electrode Renal Denervation Catheter, Medgadget (2013).
Xu, J. et al, "A Bidirectional Neuromodulation Technology for Nerve Recording and Stimulation, Micromachines," vol. 9, 1 1 538. Oct. 23, 2018. doi:10.3390/mi9110538.
Xu, J., T. Wu and Z. Yang, "A New System Architecture for Future Long-Term High-Density Neural Recording," IEEE Transactions on Circuits and Systems II: Express Briefs, vol. 60, No. 7, pp. 402-406, Jul. 2013. doi:10.1109/ TCSII.2013.2258270.
Zazgornik, "Bilateral Nephrectomy: The best, but often overlooked, treatment for refractory hypertension in hemodialysis patients," Am. J. Hypertension, 11:1364-1370 (1998).
Ziegler et al., Sources of Urinary Catecholamines in Renal Denervated Transplant Recipients, 8 J. Hypertension No. 10, 927 (1990).
U.S. Appl. No. 17/453,636, filed Nov. 4, 2021.
U.S. Appl. No. 10/408,665.
U.S. Appl. No. 60/624,793.
U.S. Appl. No. 60/370,190.
U.S. Appl. No. 60/415,575.
U.S. Appl. No. 60/442,970.
U.S. Appl. No. 60/616,254.
U.S. Appl. No. 60/816,999.
U.S. Appl. No. 14/683,966, Non Final Office Action dated Jun. 12, 2017, 14 pgs.
U.S. Appl. No. 14/683,966, Response filed Nov. 10, 2017 to Non Final Office Action dated Jun. 12, 2017, 13 pgs.
U.S. Appl. No. 14/683,966, Notice of Allowance dated Jan. 31, 2018, 8 pgs.
U.S. Appl. No. 14/683,966, PTO Response to Rule 312 Communication dated Mar. 29, 2018, 2 pgs.
U.S. Appl. No. 14/683,966, 312 Amendment filed Mar. 13, 2018, 10 pgs.
U.S. Appl. No. 14/683,966, Corrected Notice of Allowance dated May 22, 2018, 4 pgs.
U.S. Appl. No. 15/204,349, Preliminary Amendment filed Nov. 30, 2016, 3 pgs.
U.S. Appl. No. 15/204,349, Restriction Requirement dated May 17, 2018, 7 pgs.
U.S. Appl. No. 15/204,349, Response filed Jun. 5, 2018 to Restriction Requirement dated May 17, 2018, 7 pgs.
U.S. Appl. No. 15/204,349, Non Final Office Action dated Nov. 27, 2018, 14 pgs.
U.S. Appl. No. 15/204,349, Response filed Feb. 27, 2019 to Non Final Office Action dated Nov. 27, 2018, 10 pgs.
U.S. Appl. No. 15/204,349, Final Office Action dated Apr. 22, 2019, 16 pgs.
U.S. Appl. No. 15/204,349, Response filed Jun. 24, 2019 to Final Office Action dated Apr. 22, 2019, 12 pgs.
U.S. Appl. No. 15/204,349, Advisory Action dated Jul. 9, 2019, 5 pgs.
U.S. Appl. No. 15/299,694, Restriction Requirement dated Aug. 6, 2018, 6 pgs.
U.S. Appl. No. 15/299,694, Response filed Oct. 8, 2018 to Restriction Requirement dated Aug. 6, 2018, 7 pgs.
U.S. Appl. No. 15/299,694, Non Final Office Action dated Nov. 27, 2018, 15 pgs.
U.S. Appl. No. 15/299,694, Response filed Feb. 27, 2019 to Non-Final Office Action dated Nov. 27, 2018, 10 pgs.
U.S. Appl. No. 15/299,694, Final Office Action dated Apr. 22, 2019, 16 pgs.
U.S. Appl. No. 15/299,694, Response filed Jun. 24, 2019 to Final Office Action dated Apr. 22, 2019, 11 pgs.
U.S. Appl. No. 15/299,694, Advisory Action dated Jul. 9, 2019, 5 pgs.
U.S. Appl. No. 15/943,354, Preliminary Amendment filed Apr. 3, 2018, 9 pgs.
U.S. Appl. No. 15/943,354, Restriction Requirement dated Nov. 20, 2019, 8 pages.
U.S. Appl. No. 15/943,354, Response filed Dec. 19, 2019 to Restriction Requirement dated Nov. 20, 2019, 8 pages.
U.S. Appl. No. 15/943,354, Non Final Office Action dated Jan. 13, 2020, 6 pages.
U.S. Appl. No. 15/943,354, Non Final Office Action dated Apr. 20, 2020, 7 pages.
U.S. Appl. No. 15/996,978, Preliminary Amendment filed Jun. 5, 2018, 11 pgs.
U.S. Appl. No. 15/996,978, Restriction Requirement dated Feb. 7, 2020, 7 pages.
U.S. Appl. No. 15/996,978, Response filed Apr. 6, 2020 to Restriction Requirement dated Feb. 7, 2020, 8 pages.
U.S. Appl. No. 15/996,978, Restriction Requirement dated Apr. 16, 2020, 8 pages.
U.S. Appl. No. 15/996,978, Response filed May 1, 2020 to Restriction Requirement dated Apr. 16, 2020, 8 pgs.
U.S. Appl. No. 15/996,978, Non Final Office Action dated Jun. 11, 2020, 8 pages.
U.S. Appl. No. 16/517,180, Preliminary Amendment filed Jul. 19, 2019, 12 pgs.

(56) References Cited

OTHER PUBLICATIONS

File History of U.S. Appl. No. 12/754,337.
File History to U.S. Pat. No. 9,943,666.
File History to U.S. Pat. No. 9,981,108.
File History to U.S. Pat. No. 10,039,901.
Final Office Action dated Feb. 19, 2021, U.S. Appl. No. 15/996,978, filed Jun. 4, 2018.
Final Office Action dated Jun. 16, 2021, U.S. Appl. No. 15/996,978, filed Jun. 4, 2018.
Non-final Office Action dated Sep. 2, 2021, U.S. Appl. No. 15/996,978, filed Jun. 4, 2018.
Notice of Allowance dated Oct. 6, 2021, U.S. Appl. No. 15/996,978, filed Jun. 4, 2018.
Response to Office Action dated May 18, 2021, U.S. Appl. No. 15/996,978, filed Jun. 4, 2018.
Response to Office Action dated Jul. 20, 2021, U.S. Appl. No. 15/996,978, filed Jun. 4, 2018.
Response to Office Action dated Sep. 22, 2021, U.S. Appl. No. 15/996,978, filed Jun. 4, 2018.
Berjano, E., et al., "A Cooled Intraesophageal Balloon to Prevent Thermal Injury during Endocardial Surgical Radiofrequency Ablation of the left Atrium: a finite element study." Physics in Medicine and Biology, 50(20): 269-279, 2015.
Billard, B.E., et al., "Effects of Physical Parameters on High Temperature Ultrasound Hyperthermia," Ultrasound in Med. & Biol. vol. 16, No. 4, pp. 409-420, 1990.
Chapelon, J.Y., "Treatment of Localised Prostate Cancer with Transrectal High Intensity Focused Ultrasound, "European Journal of Ultrasound 9, 31-38, 1999.
Coates, Paul et al., "Time, Temperature, Power, and Impedance Considerations for Radiofrequency Catheter Renal Denervation," Cardiovascular Revascularization Medicine 42, 171-177 (2022).
Deardorff, Dana et al., Ultrasound Applicators with Internal Cooling for Interstitial Thermal Therapy, SPIE vol. 3594, 36-46, Jan. 1999.
Diederich, et al., "Catheter-based Ultrasound Applicators for Selective Thermal Ablation: progress towards MRI-guided applications in prostate," International Journal of Hyperthermia, 20:7, 739-756.
Diederich, et al., "Transurethral Ultrasound Applicators with Directional Heating Patterns for Prostate Thermal Therapy: In vivo evaluation using magnetic resonance thermometry," Med. Phys. 31 (2), 405-413, Feb. 2004.
European Search Report dated Nov. 19, 2018 in European Patent Application No. 218186547.
Fan, Xiaobing, et al., "Control of the Necrosed Tissue Volume during Noninvasive Ultrasound Surgery using a 16-Element Phased Array," Department of Radiology, Brigham and Women's Hospital, Harvard Medical School, Oct. 31, 1994.
Foley, Jessica L., et al., "Image-Guided HIFU Neurolysis of Peripheral Nerves to Treat Spasticity and Pain," Ultrasound in Med & Biol., vol. 30, Np. 9 pp. 1199-1207, 2004.
Papadopoulos, N., "Evaluation of a Small Flat Rectangular Therapeutic Ultrasonic Transducer Intended for Intravascular Use," Ultrasonics 74, 196-203, 2017.
Prakash, Punit, et al., "Considerations for Theoretical Modeling of Thermal Ablation with Catheter-Based Ultrasonic Sources: Implications for Treatment Planning, Monitoring and Control," International Journal of Hyperthermia, 28:1, 69-86.
Reddy, Vivek Y., "Use of a Diode Laser Balloon Ablation Catheter to Generate Circumferential Pulmonary Venous Lesions in an Open-Thoracotomy Caprine Model," PACE, vol. 27, 52-57, Jan. 2004.
Sato, Yu, et al., "Translational Value of Preclinical Models for Renal Denervation: a histological comparison of human versus porcine renal nerve anatomy," EuroIntervention, 18, e1120-e1128, 2023.
Ulmsten, Ulf et al., "The Safety and Efficacy of MenoTreat™, a new balloon device for thermal endometrial ablation," Acta Obstet Gynecol Scand 2001; 80: 52-57.
U.S. Appl. No. 60/747,137, File History.
U.S. Appl. No. 60/808,306, File History.
U.S. Appl. No. 61/405,472, File History.

* cited by examiner

ABLATION DEVICE WITH OPTIMIZED INPUT POWER PROFILE AND METHOD OF USING THE SAME

CROSS REFERENCE TO RELATED APPLICATIONS

The present application is a divisional application of U.S. patent application Ser. No. 12/227,508, filed Feb. 3, 2010, now U.S. Pat. No. 10,499,937, which is a national phase application of PCT/US2007/011346, filed May 10, 2007, which claims benefit of U.S. Provisional Application No. 60/802,243, filed May 19, 2006, the disclosures of each of which are hereby incorporated by reference herein in their entireties.

FIELD OF THE INVENTION

The present invention relates to medical procedures such as ablation and to apparatus and method for carrying out such procedures.

BACKGROUND OF THE INVENTION

Ultrasonic heating such as high intensity focused ultrasound (HIFU) is utilized for certain therapeutic applications. As disclosed in commonly assigned International Application PCT/US98/1062, published as International Publication WO/98/52465 the disclosure of which is hereby incorporated by reference herein, HIFU heating typically is conducted using an ultrasonic emitter having an array of transducers. The transducers are actuated with a drive signal so as to emit ultrasonic waves. The relative phasing of the waves is controlled by the physical configuration of the array and the phasing of the drive signal. These factors are selected so that the ultrasonic waves tend to reinforce one another constructively at a focal location. Tissue at the focal location is heated to a greater extent than tissue at other locations. As described, for example in commonly assigned U.S. Pat. No. 6,461,314 and in commonly assigned U.S. Pat. No. 6,492,614, the disclosures of which are also incorporated by reference herein, HIFU may be applied by transducer arrays such as arrays of polymeric piezoelectric transducers. These arrays can be mounted on a probe such as a catheter which can be introduced into the body, for example, as in a cavernous internal organ or within the vascular system to perform cardiac ablation.

Contraction or "beating" of the heart is controlled by electrical impulses generated at nodes within the heart and transmitted along conductive pathways extending within the wall of the heart. Certain diseases of the heart known as cardiac arrhythmias involve abnormal generation or conduction of the electrical impulses. One such arrhythmia is atrial fibrillation or "AF." Certain cardiac arrhythmias can be treated by deliberately damaging the tissue of the cardiac wall along a path crossing a route of abnormal conduction. This results in formation of a scar extending along the path where tissue damage occurred. The scar blocks conduction of the electrical impulses. Such a scar can be created by conventional surgery, but this entails all of the risks and expense associated with cardiac surgery. Alternatively, the scar may be made by application of energy such as heat, radio frequency energy or ultra sonic energy to the tissue that is to be scarred. Scarring the tissue by application of energy is referred to as cardiac ablation.

Commonly assigned U.S. Pat. No. 6,635,054, the disclosure of which is incorporated by reference herein in its entirety discloses thermal treatment methods and apparatus. The disclosed apparatus includes collapsible ultrasonic reflector. The reflector incorporates a gas-filled reflector balloon, a liquid-filled structural balloon and an ultrasonic transducer disposed within the structural balloon. Acoustic energy emitted by the transducer is reflected by a highly reflective interface between the balloons and focused into an annular focal region to ablate the cardiac tissue.

Commonly assigned U.S. Patent Application Publication No. US 2004/0176757, the disclosure of which is incorporated by reference herein in its entirety, discloses cardiac ablation devices. The disclosed devices are steerable and can be moved between a normal disposition, in which the ablation region lies parallel to the wall of the heart for ablating a loop like lesion, and a canted disposition, in which the ring-like focal region is tilted relative to the wall of the heart to ablate curved-linear lesions.

Conventional methods and apparatus, including the methods and apparatus mentioned above, utilize a continuous mode power profile to ablate cardiac tissue in the treatment of atrial fibrillation. However, with the conventional methods and apparatus, the collateral tissue immediately adjacent to the intended ablation target can heat up to a temperature that may result in unwanted necrosis of untargeted collateral tissue.

This unwanted necrosis of collateral tissue results from excess temperature elevation in the targeted tissue. Conventional systems deliver power in the continuous wave (CW) mode for the entire duration of the ablation cycle which sometimes results in temperature rises in the targeted tissue in excess of that needed to create necrosis. Heat from the target tissue is conducted to nearby collateral tissue and anatomical structures such as the phrenic nerve and esophagus. If the amount of heat energy is sufficiently high, than heat conducted from the targeted tissue to the collateral tissue results in elevated collateral tissue temperature sufficient to create unwanted necrosis.

Thus, there remains an unmet need for an optimized power delivery profile that quickly elevates the targeted tissue to temperatures resulting in necrosis, then maintains that temperature at a constant or near constant level for a period of time needed to achieve complete targeted tissue necrosis while, at the same time, ensures that heat conducted to adjacent collateral structures remain insufficient to cause unwanted or untargeted necrosis.

SUMMARY OF THE INVENTION

One aspect of the present invention provides a method for applying energy within the body of a living subject. The method includes providing at least one energy emitter adapted to emit energy that impinges on a tissue within the body. The method further includes providing continuous power to the energy emitter for a first duration sufficient to reach a first temperature that is equal to or higher than the temperature necessary for necrosis of the tissue. Then, during a second state, the power to the energy emitter is switched on and off to substantially maintain the tissue at a second temperature.

A method according to a related aspect of the invention includes the steps of providing at least one energy emitter and directing the output of the energy emitter on a tissue within the body. The energy emitter is connected to power and the power turned on to emit energy at a first power level, for a first duration. The first duration is sufficient to reach a first temperature in the tissue, and the first temperature is equal to or higher than the temperature necessary for necrosis of the tissue. Next, the power is switched to emit energy at a lower power level. The lower power level is sufficient to substantially maintain the tissue at a second temperature.

Another aspect of the present invention provides an apparatus for applying energy within the body of a living subject. The apparatus includes an ultrasonic emitter and a housing for the ultrasonic emitter. The housing is adapted to place the ultrasonic emitter so that the output from the emitter will be directed to a tissue within the body. A power supply is connected to the ultrasonic emitter. The power supply is adapted to supply power to the ultrasonic emitter and thereby turn it on for a first duration sufficient for a tissue to reach a first temperature that is equal to or higher than the temperature necessary for necrosis of the tissue. Next, the power is cycle between on and off conditions to turn the ultrasonic emitter on and off to substantially maintain the tissue at a second temperature.

Apparatus according to further aspect of the invention includes an ultrasonic emitter and a housing for the ultrasonic emitter, the housing being adapted to place the ultrasonic emitter so that the output from the emitter will be directed to a tissue within the body. A power supply is connected to the ultrasonic emitter. The power supply is adapted to supply power to the ultrasonic emitter to emit ultrasonic energy at a first power level, for a first duration, the first duration being sufficient to reach a first temperature in the tissue, the first temperature being equal to or higher than the temperature necessary for necrosis of the tissue. Next, the ultrasonic emitter is powered to emit at a lower power level, the lower power level being sufficient to substantially maintain the tissue at a second temperature.

DETAILED DESCRIPTION

Figure 1:
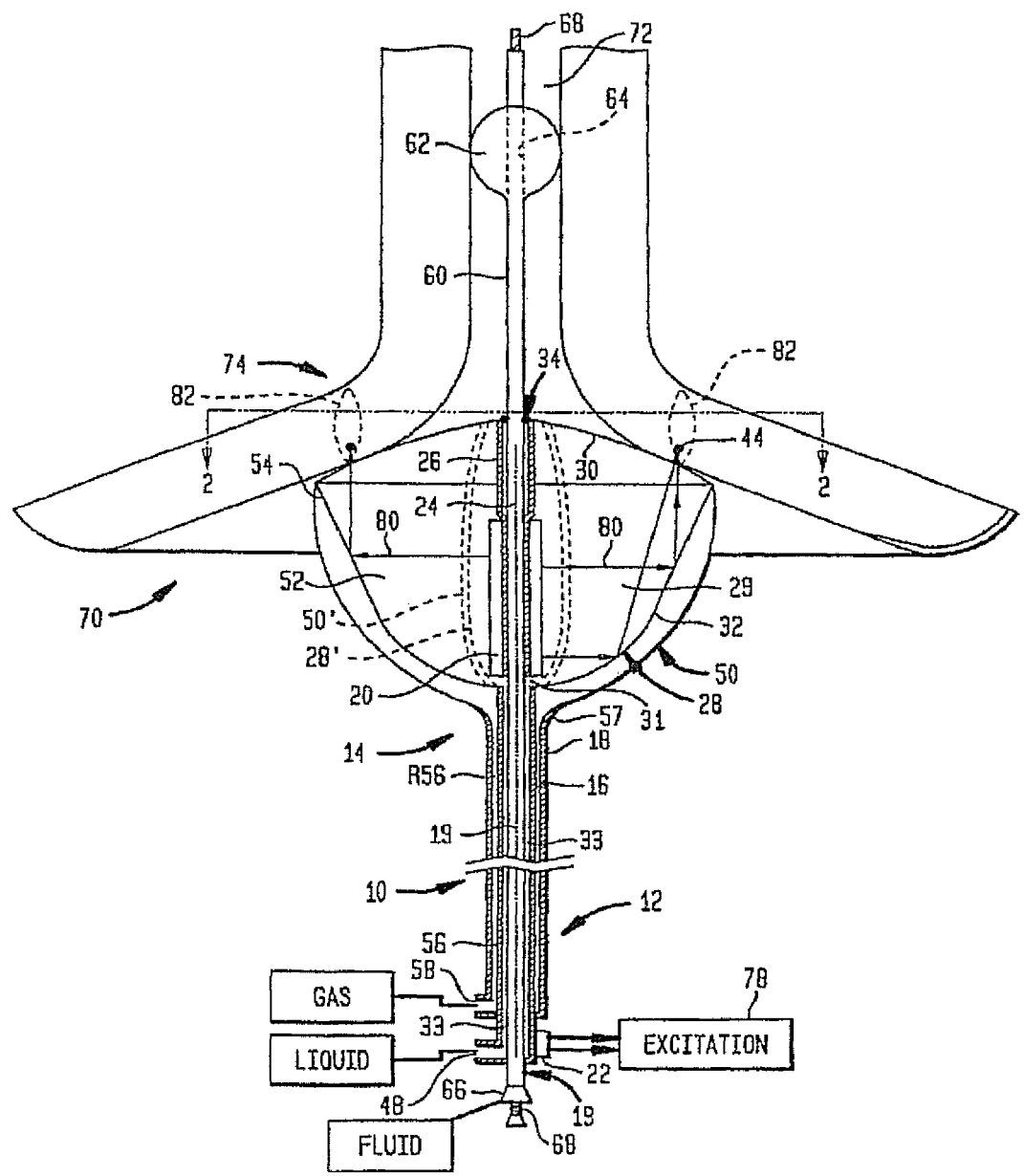
FIG. 1 is a diagrammatic view of apparatus in accordance with one embodiment of the invention in conjunction with a portion of a heart and pulmonary vein.

FIG. 1 shows one embodiment of ablation device of the invention. Many more embodiments of ablation device are disclosed in commonly assigned U.S. Pat. No. 6,635,054. Each of these embodiments can be used with the invention described herein. A portion of a probe structure 10 between proximal and distal ends 12 and 14 respectively is omitted in FIG. 1 for clarity of illustration. The probe structure includes a tubular first catheter 16 and a tubular second catheter 18 surrounding first catheter 16.

First catheter 16 and a cylindrical transducer 20 define a central axis 24 adjacent the distal end of the probe structure. First catheter 16 has a distal tip 26 projecting distally beyond transducer 20. A first balloon 28, also referred to herein as a "structural balloon," is mounted to first catheter at the distal end thereof. First balloon 28 includes an active wall 32 formed from film which is flexible but which can form a substantially noncompliant balloon structure when inflated. A forward wall 30 may be generally conical or dome-shaped and may project forwardly from its juncture with active wall 32. For example, forward wall 30 may be conical, with an included angle of about 120 degrees. Forward wall 30 joins the wall of first catheter 16 at distal tip 26 thereof, whereas active wall 32 joins the wall of catheter 16 proximally of transducer 20. Thus, transducer 20 is disposed inside of first balloon 28.

Figure 3:
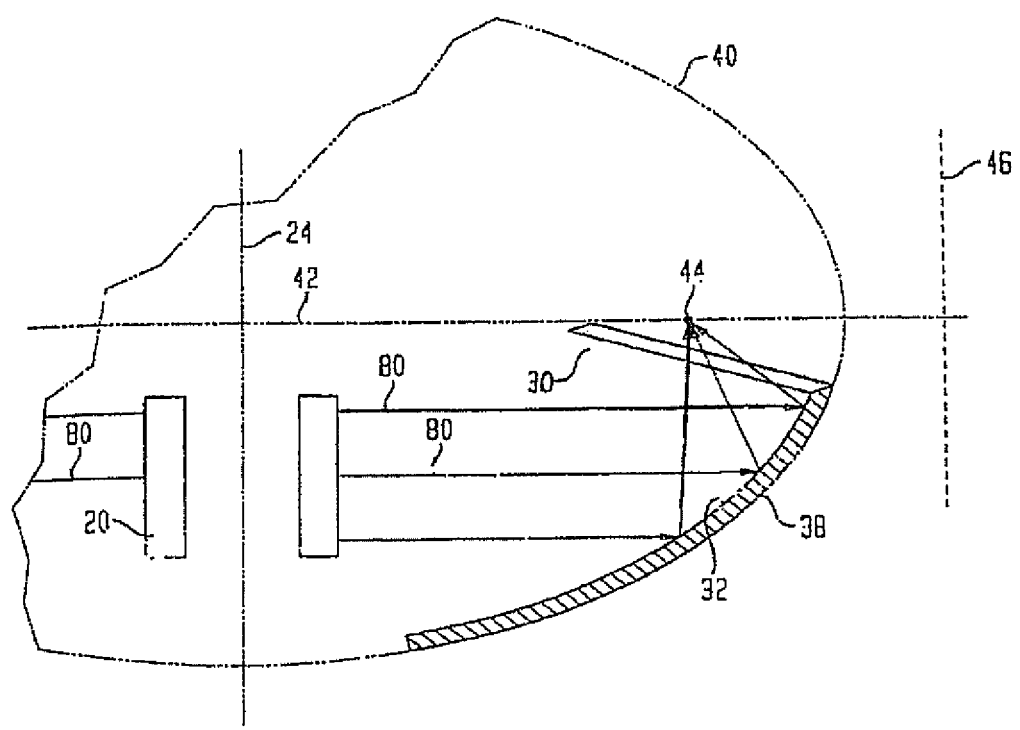
FIG. 3 is a fragmentary diagrammatic view depicting certain geometrical relationships in the apparatus of FIG. 1.

The shape of active wall region 32 depicted in FIG. may be that of a surface of revolution about central axis 24 formed by rotation of a generatrix or curve 38 (FIG. 3) which is a portion of a parabola 40 having its principal axis 42 transverse to and desirably perpendicular to central axis 24. Focus 44 of the parabolic generatrix is slightly forward or distal of forward wall 30 when the balloon is in the inflated condition.

A second balloon 50, also referred to herein as the "reflector balloon," is carried on the distal end of second catheter 18. When both first and second balloons 28 and 50, respectively, are in a deflated position, second balloon 50 is collapsed inwardly, toward central axis 24 so that second balloon in deflated condition 50' closely overlies deflated first balloon 28'.

In use, the probe structure, with first balloon 28 and second balloon 50 deflated, is threaded through the subject's circulatory system. Thereafter, upon inflation of first balloon 28 and second balloon 50, forward wall 30 of first balloon 28 bears on the interior surface of the heart wall at an ostium or opening 74 at which pulmonary vein 72 communicates with heart chamber 70.

Figure 2:
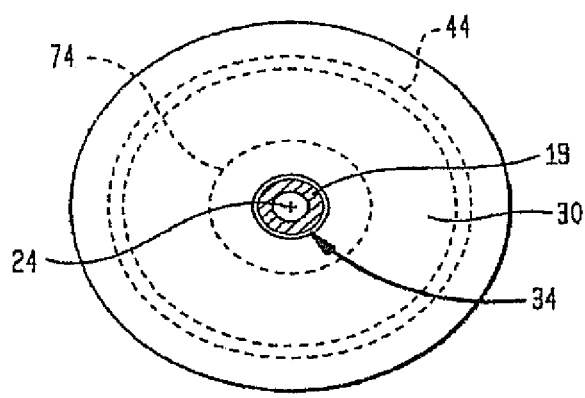
FIG. 2 is a diagrammatic sectional view taken along line 2-2 in FIG. 1.

Transducer 20 is connected to a source 78 of electrical excitation signals through connector 22. Source 78 is adapted to provide continuous and intermittent electrical excitation. Thus, Source 76 can provide continuous excitation for a predetermined period of time and then turn the electrical excitation on and off for a predetermined period of time. For example, after providing continuous excitation for between 5 and 30 seconds, source 78 may turn the electrical excitation off for a one second and then turn it on for one second and repeat the on-off cycle for a predetermined period of time. The electrical excitation actuates transducer 20 to produce ultrasonic waves. The ultrasonic waves propagate substantially radially outwardly as indicated by arrows 80 in FIGS. 1 and 3. Stated another way, cylindrical transducer 20 produces substantially cylindrical wave fronts which propagate generally radially outwardly. These waves are reflected by the interface at active region 32. Because the interface has a parabolic shape, the waves striking any region of the interface will be reflected substantially to focus 44 defined by the surface of revolution, i.e., into a substantially annular or ring-like focal region at focus 44. As best seen in FIG. 2, this ring-like focus surrounds central axis 24 and surrounds ostium 74 of the pulmonary vein. This focal region is slightly forward of forward wall 30 and hence within the heart tissue, near the surface of the heart wall. For example, the focal region may be disposed at a depth equal to about one-half of the thickness of the heart wall as, for example, about 2-4 mm from the surface of the wall.

The heart wall tissue located at focus 44 is heated rapidly. The initial CW power delivery Is performed with high power output to quickly create the initial lesion which creates an absorptive barrier for ultrasound and therewith protects distal collateral structures. It is believed that the lesion will mostly grow towards the source. The temperature of the tissue depends upon several factors including the output power of transducer 20 and the time for which the tissue is exposed to the output of transducer 20. Upon the target tissue being exposed to the ultrasonic output of transducer 20 for a predetermined time, the target tissue reaches the target temperature, i.e., the temperature that would result in necrosis. The target temperature may be in the range 55-80 degrees centigrade, preferably in the range 55-60 degrees centigrade. The continuous excitation is maintained for a first duration sufficient for the target tissue to reach the target temperature. At the end of the first duration, the electrical excitation is turned on and off to maintain the target tissue at the target temperature. The rapid heating of the target tissue to the target temperature effectively ablates or kills the tissue at the focal region so that a wall of non-conductive scar tissue forms in the focal region and in neighboring tissue. However, by turning the electrical excitation on and off and thereby maintaining the target tissue at the target temperature, the amount of neighboring tissue that is killed is minimized. This is in contrast to keeping the electrical excitation on continuously for the entire duration of time necessary to ablate the target tissue. If the electrical excitation is kept on for the entire duration of time necessary to ablate the target tissue, the temperature of the target tissue keeps rising for the entire duration and exceeds the temperature necessary for tissue necrosis. This results in necrosis of greater amount of neighboring tissue as compared to when the electrical excitation is turned on and off during the ablation cycle. For a particular ablation apparatus using particular transducer, the time it takes for the target tissue to reach the target temperature may be determined via theoretical models or experimentally or by a combination of these techniques. For a given ablation apparatus, experiments may be carried out wherein the cardiac tissue is ablated and temperature of the tissue at different time measured by known techniques such as use of thermocouples or imaging. Based upon these experiments, a recommendation for duration of operation of the ablation apparatus in the continuous mode and duration of operation in the on-off mode would be provided to the physicians. The process will have to be repeated for an ablation apparatus of a different design.

Figure 4:
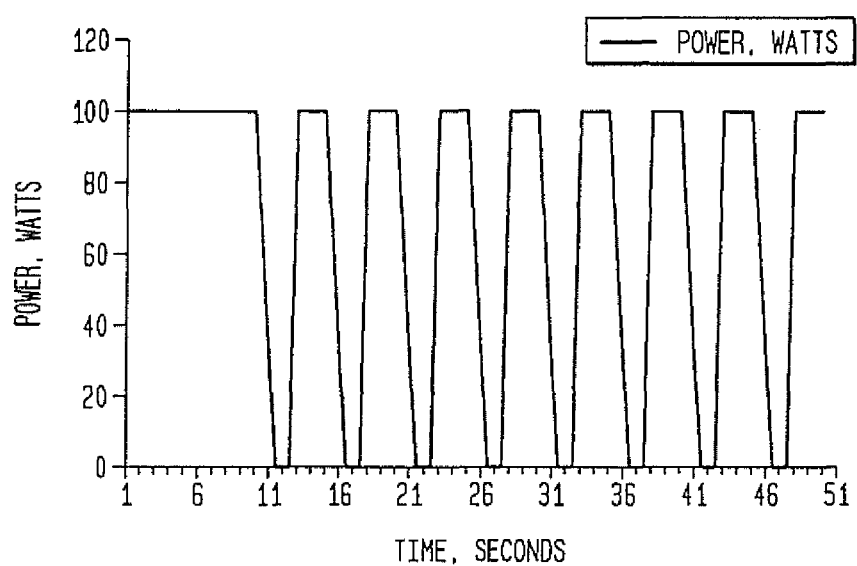
FIG. 4 is an example of input power profile for the apparatus of FIG. 1.

FIG. 4 shows the input power profile for electrical excitation of transducer 20. At the beginning of the ablation cycle, transducer 20 is supplied with 100 watt electrical excitation signal. The excitation of transducer 20 is continuous for approximately 11 seconds. However, the continuous excitation mode may range from 5 seconds to 30 seconds or for the duration necessary for the target tissue to reach the target temperature. Once the target tissue has reached the target temperature the input power is cycled off and on as shown in FIG. 4. The power is off for roughly 25 percent of the time and the power is on for roughly 75 percent of the time. To put it another way, once the target tissue has reached the target temperature, the power is off for roughly 1 second and then it is on for roughly 3 seconds with the on-off cycle continuing for the duration of the ablation cycle. The power is turned off at the end of the ablation cycle and the temperature of the target tissue drops rapidly thereafter. It should be noted that the power on-off cycle can be varied, for example, similar results may be obtained with the power being off for one second and on for one second following the continuous excitation mode. Alternatively, the entire power input profile may consist of continuous excitation at one power level and upon reaching of the target temperature switching to continuous excitation at a second lower power level.

Figure 5:
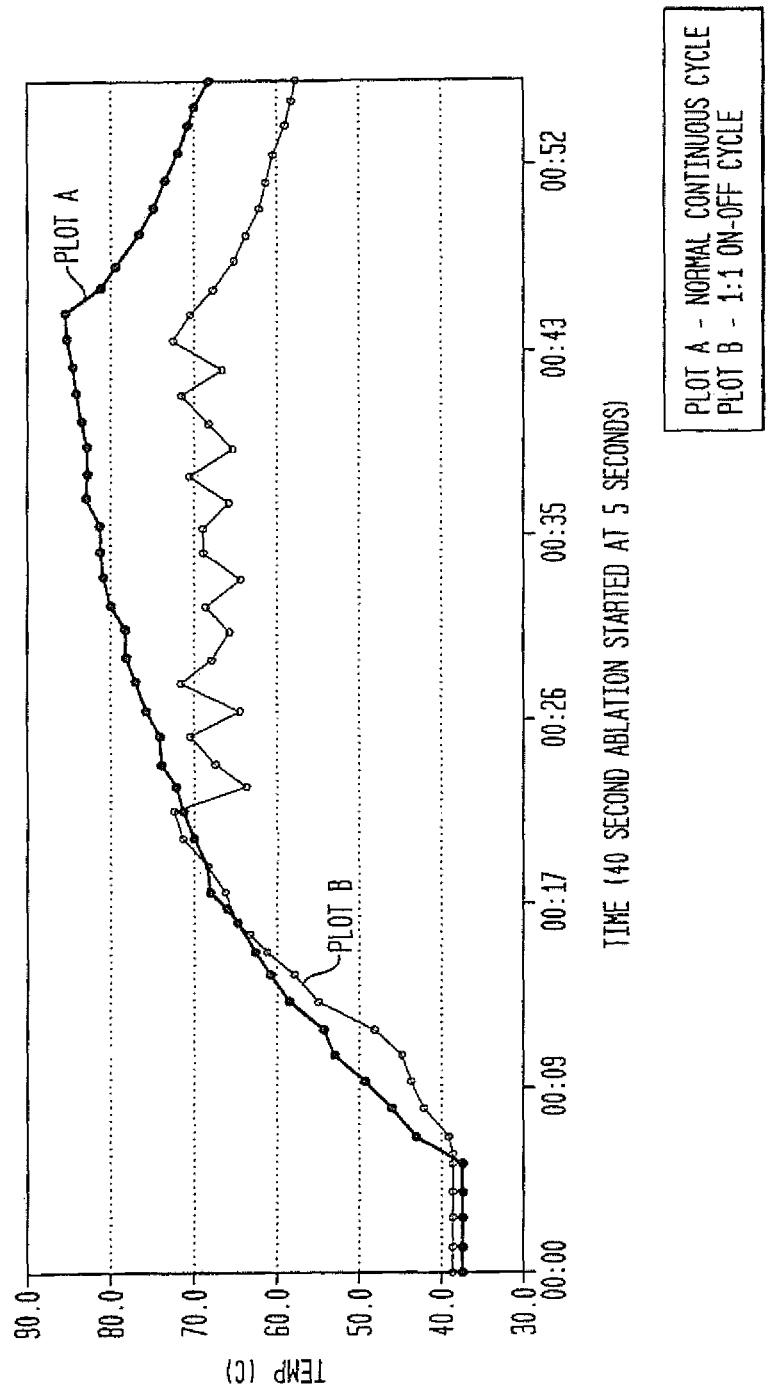
FIG. 5 is a graph of temperature (at the phrenic nerve) versus time measured during animal experiments.

FIG. 5 shows plots of temperature measured at a fixed distance from the target tissue during animal experiments. A 20 mm HIFU Ablation Catheter made by Prorhythm, inc., was used. The Ablation catheter was supplied with 100 watt electrical excitation signal, and the HIFU output was 32 watts acoustic. A 20 mm ablation device kills tissue in the shape of a ring of 20 mm diameter. Several embodiments of ablation devices that can cause necrosis of tissue in shape of a ring are disclosed in U.S. Pat. No. 6,635,054 and U.S. Patent Application Publication No. US 2004/0176757. As seen in FIG. 5, plot A, the temperature at the fixed distance from the target tissue keeps rising for the entire duration of the ablation cycle when the electrical excitation is kept on for the entire duration of the ablation cycle. On the other hand, as seen in FIG. 5, plot B, when the electrical excitation is turned on and off during a portion of the ablation cycle, the temperature at the fixed distance from the target tissue rises during the continuous excitation mode and then remains substantially constant at that level during the on-off mode. This results in reduction or elimination of collateral tissue damage.

Some of the ultrasonic energy is absorbed between the surface of the wall and the focal region, and at locations deeper within the wall than the focal region. To provide a complete conduction block, tissue should be ablated through the entire thickness of the wall, so as to form a transmural lesion. With a transducer capable of emitting about 15 Watts of acoustic energy, an ablated region extending entirely through the heart wall can be formed within a few minutes of actuation. Higher power levels as, for example, above 30 Watts of acoustic energy and desirably about 45 Watts are preferred because such power levels will provide shorter lesion formation time (under one minute). Because the sonic energy is directed simultaneously into the entire loop-like path surrounding the pulmonary vein, the PV isolation can be performed ideally without repositioning the probe. However, several applications may be required due to non circular, irregular anatomy.

The positioning of the ablation device within the heart desirably includes selectively controlling the disposition of the forward-to-rearward axis 24 of the device relative to the patient's heart. That is, the position of the forward-to-rearward axis desirably can be controlled by the physician to at least some degree. To that end, the assembly can be provided with one or more devices for selectively bending the ablation device. Various embodiments of the ablation device that lend themselves to allow disposition of the ablation device to be selectively controlled are disclosed in commonly assigned Patent Application No. US 2004/0176757. Each of these embodiments may be used in conjunction with the input power profile disclosed herein. Although the invention has been described with the aid of an ablation device using HIFU, any form of output power for ablating the tissue may be used in the on-off mode as described herein to realize the benefit of the invention. Non limiting examples of the other forms of output power are RF and heat.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

INDUSTRIAL APPLICABILITY

This application relates to the medical device industry.

What is claimed:

1. An apparatus for applying energy intraluminally to a target tissue, the apparatus comprising:
a catheter having a distal region adapted for placement adjacent to a tissue wall, wherein the tissue wall is between the distal region and the target tissue;
a balloon disposed at the distal region of the catheter;
an ultrasound transducer disposed within the balloon, wherein the ultrasound transducer emits ultrasonic energy through the balloon to the target tissue in response to being electrically excited;
an energy emission source configured to electrically excite the ultrasound transducer continuously during a first time duration and cyclically during a second time duration, wherein electrical excitation of the ultrasound transducer is continuously turned on during the first time duration to ablate a first portion of the target tissue without ablating a second portion of the target tissue between the first portion and the tissue wall, wherein electrical excitation of the ultrasound transducer is cyclically turned on and off during the second time duration to ablate the second portion of the target tissue between the first portion and the tissue wall and to minimize ablation of distal collateral tissue adjacent to the first portion of the target tissue, and wherein the first time duration and the second time duration are based on the ultrasound transducer used to emit the ultrasonic energy through the balloon and based on an empirical determination of a temperature of the target tissue without monitoring the temperature of the target tissue.

2. The apparatus of claim 1, further comprising a reflector at the distal region of the catheter, the reflector having an active region to redirect energy from the ultrasound transducer, wherein the active region defines a focal region comprising a volume of the target tissue.

3. The apparatus of claim 2, wherein the reflector includes an active wall of the balloon.

4. The apparatus of claim 3, wherein the active wall includes a surface of revolution about a central axis of the ultrasound transducer.

5. The apparatus of claim 2, wherein the reflector is parabolic in shape and causes the active region to define a circular focal region.

6. The apparatus of claim 1, wherein the distal region of the catheter is adapted for placement within a blood vessel.

7. The apparatus of claim 1, wherein the ultrasonic energy is continuously emitted at a first power level during the first time duration, wherein the ultrasonic energy is cyclically emitted at the first power level and a second power level during the second time duration, and wherein the first power level is greater than the second power level.

8. The apparatus of claim 7, wherein no ultrasonic energy is delivered at the second power level.

9. An apparatus for applying energy intraluminally to a target tissue, the apparatus comprising:
a catheter having a distal region adapted for placement adjacent to a tissue wall, wherein the tissue wall is between the distal region and the target tissue; and
an ultrasound transducer disposed at the distal region of the catheter, wherein the ultrasound transducer emits ultrasonic energy in response to being electrically excited; and
an energy emission source configured to electrically excite the ultrasound transducer continuously during a first time duration and cyclically during a second time duration, wherein electrical excitation of the ultrasound transducer is continuously turned on during the first time duration to ablate a first portion of the target tissue without ablating a second portion of the target tissue between the first portion and the tissue wall, wherein electrical excitation of the ultrasound transducer is cyclically turned on and off during the second time duration to ablate the second portion of the target tissue between the first portion and the tissue wall and to minimize ablation of distal collateral tissue adjacent to the first portion of the target tissue, and wherein the first time duration and the second time duration are based on the ultrasound transducer used to emit the ultrasonic energy and based on an empirical determination of a temperature of the target tissue.

10. The apparatus of claim 9, wherein the target tissue comprises a transmural area of an organ or a blood vessel.

11. The apparatus of claim 9, wherein the distal region of the catheter is adapted for placement within a blood vessel.

12. The apparatus of claim 9, wherein the ultrasonic energy is continuously emitted at a first power level during the first time duration, wherein the ultrasonic energy is cyclically emitted at the first power level and a second power level during the second time duration, and wherein the first power level is greater than the second power level.

13. The apparatus of claim 12, wherein no ultrasonic energy is delivered at the second power level.

14. The apparatus of claim 9, wherein the first time duration and the second time duration are based on the empirical determination without monitoring the temperature of the target tissue.

15. The apparatus of claim 9, wherein the first portion of the target tissue provides a protective barrier to reduce damage to untargeted tissue during the second time duration.

16. The apparatus of claim 9, further comprising the energy emission source is configured to provide electrical energy to the ultrasound transducer.

17. The apparatus of claim 9, further comprising a balloon disposed at the distal region of the catheter, wherein the ultrasound transducer is disposed within the balloon.

18. The apparatus of claim 9, further comprising a reflector at the distal region of the catheter, the reflector having an active region to redirect ultrasonic energy from the ultrasound transducer, wherein the active region defines a focal region comprising a volume of the target tissue.

19. The apparatus of claim 18, wherein the reflector is parabolic in shape and causes the active region to define a circular focal region.

20. The apparatus of claim 1, wherein the ultrasound transducer is turned on for 50-75% of the second time duration.

* * * * *